United States Patent
Garcia-Moreno et al.

(10) Patent No.: US 10,138,471 B2
(45) Date of Patent: Nov. 27, 2018

(54) INSERTION OF CHARGE IN THE HYDROPHOBIC INTERIOR OF PROTEINS AS A STRATEGY FOR ENGINEERING PH-SENSITIVE SWITCHES

(71) Applicant: The Johns Hopkins University, Baltimore, MD (US)

(72) Inventors: Bertrand E. Garcia-Moreno, Baltimore, MD (US); Aaron Robinson, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 516 days.

(21) Appl. No.: 14/507,381

(22) Filed: Oct. 6, 2014

(65) Prior Publication Data

US 2015/0099290 A1    Apr. 9, 2015

Related U.S. Application Data

(60) Provisional application No. 61/887,099, filed on Oct. 4, 2013.

(51) Int. Cl.
C12N 9/22    (2006.01)

(52) U.S. Cl.
CPC ........ *C12N 9/22* (2013.01); *C12Y 301/31001* (2013.01)

(58) Field of Classification Search
CPC ......... G06F 19/16; G06F 19/12; C11D 3/386; C07K 14/31; C07K 1/107
See application file for complete search history.

(56) References Cited

U.S. PATENT DOCUMENTS

| 6,385,546 B1 | 5/2002 | Kahn et al. |
| 2012/0258518 A1 | 10/2012 | Garcia-Moreno et al. |

FOREIGN PATENT DOCUMENTS

WO    2011069017 A1    6/2011

OTHER PUBLICATIONS

Non-Final Office Action dated Jan. 7, 2014 issued to the related U.S. Appl. No. 13/513,259.
Chen et al., "Increasing the Thermostability of *Staphylococcal nuclease*: Implications for the Origin of Protein Thermostability", J. Mol. Biol. (2000) 303:125-130.
Final Office Action dated Sep. 15, 2014 issued to the related U.S. Appl. No. 13/513,259.
Isom et al., "High tolerance for ionizable residues in the hydrophobic interior of proteins", PNAS, Nov. 18, 2008, 105(46):17784-17788.
Hollien et al., "A Thermodynamic Comparison of Mesophilic and Thermophilic Ribonucleases H", Biochemistry 1999, 38, 3831-3836.
Non-Final Office Action dated May 19, 2015 issued to the related U.S. Appl. No. 13/513,259.
Dao-Pin et al., "Structural and Thermodynamic Consequences of Burying a Charged Residue within the Hydrophobic Core of T4 Lysozyme", Biochemistry, 1991, 30:11521-11529.
Final Office Action dated Feb. 11, 2016 issued to the related U.S. Appl. No. 13/513,259.
Denisov et al., Stabilization of Internal Charges in a Protein: Water Penetration or Conformational Change Biophysical Journal, 2004, vol . 87, No. 6, pp. 3982-3994.
Byrne et al., Energetic contribution of side chain hydrogen bonding to the stability of *Staphylococcal nuclease.*, Biochemistry, 1995, vol . 34, No. 42, pp. 13949-13960.
European Search Report dated Jul. 16, 2014 from European Application No. 10835157.8-1453/2507631 PCT/US2010/058800.
Harms MJ, et al. (2009) The pKa values of acidic and basic residues buried at the same internal location in a protein are governed by different factors. J Mol. Biol. 389: 34-47.
Fitch CA, et al. (2002) Experimental pKa values of buried residues: analysis with continuum methods and role of Water penetration. Biophysical Journal 82: 3289-3304.
Zheng L, Mengen C, & Yang W (2008) Random walk in orthogonal space to achieve efficient free-energy simulation of complex systems. Proc. Natl. Acad. Sci. USA 105: 20227-20232.
Isom DG, et al. (2008) High tolerance for ionizable residues in the hydrophobic interior of proteins. Proc. Natl. Acad. Sci. USA 105: 17784-17788.
Thurlkill RL, Grimsley GR, Scholtz JM, & Pace CN (2006)Hydrogen Bonding Markedly Reduces the pK of Buried Carboxyl Groups in Proteins. Journal of Molecular Biology 362: 594-604.
Damjanovic A, et al. (2007) Role of flexibility and polarity as determinants of the hydration of internal cavities and pockets in proteins. Biophysical Journal 93: 2791-2804.
Schlessman JL, et al. (2008) Crystallographic study of hydration of an internal cavity in engineered proteins with buried polar or ionizable groups. Biophys. J. 94: 3208-3216.
Gong H, Hocky G, & Freed KF (2008) Influence of nonlinear electrostatics on transfer energies between liquid phases: charge burial is far less expensive than Born Model. Proc. Natl. Acad. Sci. USA 105: 11146-11151.
Nguyen DM, Reynald RL, Gittis AG, & Lattman EE (2004) X-ray and thermodynamic studies of *Staphylococcal nuclease* variants 192E and 192K: Insights into polarity of the protein interior. J Mol. Biol.: 565-574.
Karp DA, Stahley MR, & Garcia-Moreno E. B (2010) Conformational consequences of ionization of Lys, Asp, and Glu buried at position 66 in *Staphylococcal nuclease*. Biochemistry 49: 4138-4146.
Simonson T & Perahia D (1995) Internal and Interfacial Dielectric Properties of Cytochrome c from Molecular Dynamics in Aqueous Solution. Proceedings of the National Academy of Sciences of the United States of America 92: 1082-1086.
Karp et al., High apparent dielectric constant inside a protein reflects structural reorganization coupled to the ionization of an internal Asp. Biophys. J. 2007, vol. 92, No. 6, pp. 2041-2053.

(Continued)

*Primary Examiner* — Kagnew H Gebreyesus
(74) *Attorney, Agent, or Firm* — Casmir Jones, S.C.; Jeffrey W. Childers

(57) ABSTRACT

Methods are provided for engineering non-naturally occurring proteins comprising artificial pH-sensitive conformational switches that respond to a change in pH by causing a global unfolding of the proteins. Non-naturally occurring proteins comprising artificial pH-sensitive conformational switches that respond to a change in pH by causing a global unfolding of the proteins are also provided.

5 Claims, 16 Drawing Sheets

Specification includes a Sequence Listing.

(56) References Cited

OTHER PUBLICATIONS

Harms et al., A buried lysine that titrates with a normal pKa; role of conformational flexibility at the protein-water interface as a determinant of pKa values, Protein Sci., 2008, vol. 17, No. 5, pp. 833-845-; abstrract; p. 842, para 2.
Ihee, H. et al. Visualizing reaction pathways in photoactive yellow protein from nanoseconds to seconds. Proc. Natl. Acad. Sci. USA 102, 7145-7150 (2005).
Lanyi, J. K. Proton transfers in the bacteriorhodopsin photocycle. BBA Bioenergetics 1757, 1012-1018 (2006).
Pisliakov, A. V., Sharma, P. K., Chu, Z. T., Haranczyk, M. & Warshel, A. Electrostatic basis for the unidirectionality of the primary proton transfer in cytochrome c oxidase. Proc. Natl. Acad. Sci. USA 105, 7726-7731 (2008).
Chen, V. B. et al. MolProbity: all-atom structure validation for macromolecular crystallography. Acta Crystallogr. D 66, 12-21 (2010).
Dwyer, J. J. et al. High Apparent Dielectric Constants in the Interior of a Protein Reflect Water Penetration. Biophys. J. 79, 1610-1620 (2000).
García-Moreno, B. E. et al. Experimental measurement of the effective dielectric in the hydrophobic core of a protein. Biophys. Chem. 64, 211-224 (1997).
Chimenti, M. S., Castañeda, C. A., Majumdar, A. & García-Moreno E., B. Structural Origins of High Apparent Dielectric Constants Experienced by Ionizable Groups in the Hydrophobic Core of a Protein. J. Mol. Biol. 405, 361-377 (2011).
Zheng, Z. & Sosnick, T. R. Protein Vivisection Reveals Elusive Intermediates in Folding. J. Mol. Biol. 397, 777-788 (2010).
McCoy, A. J., Grosse-Kunstleve, R. W., Storoni, L. C. & Read, R. J. Likelihood-enhanced fast translation functions. Acta Crystallogr. D 61, 458-464 (2005).
Emsley, P. & Cowtan, K. Coot?: model-building tools for molecular graphics. Acta Crystallogr. D 60, 2126-2132 (2004).
Vaguine, A. A., Richelle, J. & Wodak, S. J. Sfcheck: a unified set of procedures for evaluating the quality of macromolecular structure-factor data and their agreement with the atomic model. Acta Crystallogr. D 55, 191-205 (1999).
Laskowski, R. A., MacArthur, M. W., Moss, D. S. & Thornton, J. M. Procheck: a program to check the stereochemical quality of protein structures. J. Appl. Crystallogr. 26, 283-291 (1993).
International Preliminary Report on Patentability dated Apr. 12, 2016 for corresponding international application No. PCT/US2014/059338.
Rastogi, V. et al (1999) Structural changes linked to proton translocation by subunit c of the ATPase synthase. Nature 402: 263-268.
Stites, W. et al (1991) In a *staphylococcal* nuclease mutant the side-chain of a lysine replacing valine 66 is fully buried in the hydrophobic core. Journal of Molecular Biology 221: 7-14.
Ghosh, N. et al (2008) pKa of residue 66 in *Staphylococcal nuclease*. I. Insights from QM/MM simulations with conventional sampling. J Phys. Chem. B. 112: 8387-8397.
Schutz, C. et al (2001) What are the dielectric "constants" of proteins and how to validate electrostatic models? Proteins: Structure, Function, and Genetics 44: 400- 417.
Damjanovic, A. et al (2005) Molecular Dynamics Study of Water Penetration in *Staphylococcal nuclease*. Proteins: Structure Function and Bioinformatics 60: 433-449.
Ho, M. et al (2009) The origin of the electrostatic perturbation in acetoacetate decarboxylase. Nature 459: 393-399.
Bone, S. et al (1982) Dielectric studies of the binding of water to lysozyme. Journal of Molecular Biology 157: 571-575.
Bone, S. et al ( 1985) Dielectric studies of protein hydration and hydration-induced flexibility. Journal of Molecular Biology 181: 323-326.
Pey AL, et al. (2010) Modulation of buried ionizable groups in proteins with engineered surface charge. J Am. Chem. Soc. 132: 1218-1219.

Smith, P. et al (1993) Dielectric properties of trypsin inhibitor and lysozyme calculated from molecular dynamics simulations. Journal of Physical Chemistry 97: 2009-2014.
Simonson, T. et al (1996) Charge screening and the dielectric constant of proteins: Insights from molecular dynamics. Journal of the American Chemical Society 118: 8452-8458.
Varadarajan, R. et al (1989) Effects of Buried Ionizable Amino Acids on the Reduction Potential of Recombinant Myoglobin. Science 243: 69-72.
Varadajaran R, Lambright DG, Boxer SG (1989) Electrostatic Interactions in Wild-Type and Mutant Recombinant Human Myoglobins. Biochemistry 28: 3771-3781.
Shortle, D. et al (1986) Mutant forms of *Staphylococcal nuclease* with altered patterns of guanidine hydrochloride and urea denaturation. Proteins: Structure, Function, and Genetics 1: 81-89.
Whitten, S. et al (2000) pH dependence of stability of *Staphylococcal nuclease*: Evidence of substantial electrostatic interactions in the denatured state. Biochemistry 39: 14292-14304.
Castaneda CA, et al. (2009) Molecular determinants of the pKa values of Asp and Glu residues in *Staphylococcal nuclease*. Proteins: Struct. Funct. Bioin. 77: 570-588.
Anfinsen, C.B. Principles that govern folding of protein chains. Science 181: 223-230 (1973).
Bailey, S. The CCP4 suite—programs for protein crystallography. Acta Crystallogr. D 50: 760-763 (1994).
Bouvignies, G. et al. Solution structure of a minor and transiently formed state of a T4 lysozyme mutant. Nature 477: 111-114 (2011).
Cannon, B. Thermodynamic consequences of substitution of internal positions in proteins with polar and ionizable residues. Johns Hopkins University, Ph.D. Thesis, (2008).
Delaglio, F. et al. NMRPipe: A multidimensional spectral processing system based on UNIX pipes. J. Biomol. NMR 6, 277-293 (1995).
Englander, S.W. Protein Folding Intermediates and Pathways Studied by Hydrogen Exchange. Annu. Rev. Bioph. Biom. 29: 213-238 (2000).
Goddard, T. and Kneller, D. SPARKY 3. University of California, San Francisco.
Grzesiek, S., Anglister, J. and Bax, A. Correlation of Backbone Amide and Aliphatic Side-Chain Resonances in 13C/15N-Enriched Proteins by Isotropic Mixing of 13C Magnetization. J. Magn. Reson. B 101: 114-119 (1993).
Higgins, H.G. and Sharp, P.M. Fast and sensitive multiple sequence alignments on a microcomputer. CABIOS, 5:151-153 (1989).
Higgins, D.G., Bleasby, A.J., and Fuchs, R. CLUSTAL V: improved software for multiple sequence alignment. Comput. Appl. Biosci. 8:189-191 (1992).
Grzesiek, S. & Bax, A. Correlating backbone amide and side chain resonances in larger proteins by multiple relayed triple resonance NMR. J. Am. Chem. Soc. 114, 6291-6293 (1992).
Painter, J. and Merritt, E.A. TLSMD web server for the generation of multi-group TLS models. J. Appl. Crystallogr. 39: 109-111 (2006).
Perutz, M.F. Stereochemistry of Cooperative Effects in Haemoglobin: Haem-Haem Interaction and the Problem of Allostery. Nature 228: 726-734 (1970).
Shortle, D., Meeker, A.K. and Freire, E. Stability mutants of *Staphylococcal nuclease*: large compensating enthalpy—entropy changes for the reversible denaturation reaction. Biochemistry 27: 4761-4768 (1988).
Takayama Y., Castañeda C.A., Chimenti M., García-Moreno B., Iwahara J. Direct evidence for deprotonation of a lysine side chain buried in the hydrophobic core of a protein. J. Am. Chem. Soc. 130:6714-6715 (2008).
Von Ballmoos, C., Wiedenmann, A., and Dimroth, P. Essentials for ATP Synthesis by F1F0 ATP Synthases. Annu. Rev. Biochem. 78: 649-672 (2009).
Wiley, D.C. and Skehel, J.J. The Structure and Function of the Hemagglutinin Membrane Glycoprotein of Influenza Virus. Annu. Rev. Biochem. 56: 365-394 (1987).
Wittekind, M. and Mueller, L. HNCACB, a High-Sensitivity 3D NMR Experiment to Correlate Amide-Proton and Nitrogen Reso-

(56) References Cited

OTHER PUBLICATIONS nances with the Alpha- and Beta-Carbon Resonances in Proteins. J. Magn. Reson. B 101: 201-205 (1993).

Yamazaki, T., Yoshida, M., and Nagayama, K. Complete assignments of magnetic resonances of ribonuclease H from *Escherichia coli* by double- and triple-resonance 2D and 3D NMR spectroscopies. Biochemistry 32: 5656-5669 (1993).

Chimenti, M.S. et al. Structural reorganization triggered by charging of Lys Residues in the hydrophobic interior of a protein. Structure. vol. 20, Issue 6, Jun. 6, 2012, pp. 1071-1085.

Isom, D. et al. Large shifts in pKa values of lysine residues buried inside a protein. PNAS. 108(13), pp. 5260-5265, 2011.

Harms, M. et al. Arginine residues at internal positions in a protein are always charged. PNAS 108(47), pp. 18954-18959, 2011.

Isom, D. et al. Charges in the hydrophobic interior of proteins. PNAS 107(37), pp. 16096-16100, 2010.

Bizzarri et al. Green fluorescent protein based pH indicators for in vivo use: a review. Analytical and Bioanalytical Chemistry, 393:1107-1122, 2009.

Rose, G. D., Fleming, P. J., Banavar, J. R. & Maritan, A. A backbone-based theory of protein folding. Proc. Natl. Acad. Sci. USA 103, 16623-16633 (2006).

Bai, Y., Sosnick, T., Mayne, L. & Englander, S. Protein folding intermediates: native-state hydrogen exchange. Science 269, 192-197 (1995).

Hansen, D. F., Vallurupalli, P. & Kay, L. E. Using relaxation dispersion NMR spectroscopy to determine structures of excited, invisible protein states. J. Biomol. NMR 41, 113-120 (2008).

Westerheide, S. D. & Morimoto, R. I. Heat Shock Response Modulators as Therapeutic Tools for Diseases of Protein Conformation. J. Biol. Chem. 280, 33097-33100 (2005).

Dul, J. L., Davis, D. P., Williamson, E. K., Stevens, F. J. & Argon, Y. Hsp70 and Antifibrillogenic Peptides Promote Degradation and Inhibit Intracellular Aggregation of Amyloidogenic Light Chains. J. Cell Biol. 152, 705-716 (2001).

Neudecker, P. et al. Structure of an Intermediate State in Protein Folding and Aggregation. Science 336, 362-366 (2012).

Smith, D. P., Jones, S., Serpell, L. C., Sunde, M. & Radford, S. E. A Systematic Investigation into the Effect of Protein Destabilisation on Beta 2-Microglobulin Amyloid Formation. J. Mol. Biol. 330, 943-954 (2003).

Chiti, F. et al. Mutational analysis of the propensity for amyloid formation by a globular protein. EMBO J. 19, 1441-1449 (2000).

Baldwin, R. L. The Search for Folding Intermediates and the Mechanism of Protein Folding.Annu. Rev. Biophys. 37, 1-21 (2008).

Sosnick, T. R. & Barrick, D. The folding of single domain proteins—have we reached a consensus? Curr. Opin. Struc. Biol. 21, 12-24 (2011).

SEQUENCE LISTING

```
<160> NUMBER OF SEQ ID NOS: 3

<210> SEQ ID NO 1
<211> LENGTH: 149
<212> TYPE: PRT
<213> ORGANISM: Staphylococcus aureus

<400> SEQUENCE: 1

Ala Thr Ser Thr Lys Lys Leu His Lys Glu Pro Ala Thr Leu Ile Lys
1               5                   10                  15

Ala Ile Asp Gly Asp Thr Val Lys Leu Met Tyr Lys Gly Gln Pro Met
            20                  25                  30

Thr Phe Arg Leu Leu Leu Val Asp Thr Pro Glu Thr Lys His Pro Lys
        35                  40                  45

Lys Gly Val Glu Lys Tyr Gly Pro Glu Ala Ser Ala Phe Thr Lys Lys
    50                  55                  60

Met Val Glu Asn Ala Lys Lys Ile Glu Val Glu Phe Asp Lys Gly Gln
65                  70                  75                  80

Arg Thr Asp Lys Tyr Gly Arg Gly Leu Ala Tyr Ile Tyr Ala Asp Gly
                85                  90                  95

Lys Met Val Asn Glu Ala Leu Val Arg Gln Gly Leu Ala Lys Val Ala
            100                 105                 110

Tyr Val Tyr Lys Pro Asn Asn Thr His Glu Gln His Leu Arg Lys Ser
        115                 120                 125

Glu Ala Gln Ala Lys Lys Glu Lys Leu Asn Ile Trp Ser Glu Asp Asn
    130                 135                 140

Ala Asp Ser Gly Gln
145

<210> SEQ ID NO 2
<211> LENGTH: 143
<212> TYPE: PRT
<213> ORGANISM: Staphylococcus aureus

<400> SEQUENCE: 2

Ala Thr Ser Thr Lys Lys Leu His Lys Glu Pro Ala Thr Leu Ile Lys
```

```
                1               5                  10                 15
            Ala Ile Asp Gly Asn Thr Val Lys Leu Met Tyr Lys Gly Gln Pro Met
                            20                  25                 30

Val Phe Arg Leu Leu Leu Val Asp Ile Pro Glu Phe Asn Glu Lys Tyr
                            35                  40                 45

Gly Pro Glu Ala Ala Ala Phe Thr Lys Lys Met Val Glu Asn Ala Lys
                        50                  55                 60

Lys Ile Glu Val Glu Phe Asp Lys Gly Gln Arg Thr Asp Lys Tyr Gly
            65                  70                  75                 80

Arg Gly Leu Ala Tyr Ile Tyr Ala Asp Gly Lys Met Val Asn Glu Ala
                            85                  90                 95

Leu Val Arg Gln Gly Leu Ala Lys Val Ala Tyr Val Tyr Lys Gly Asn
                            100                 105                110

Asn Thr His Glu Gln Leu Leu Arg Lys Ala Glu Ala Gln Ala Lys Lys
                        115                 120                125

Glu Lys Leu Asn Ile Trp Ser Glu Asp Asn Ala Asp Ser Gly Gln
                130                 135                 140

<210> SEQ ID NO 3
<211> LENGTH: 143
<212> TYPE: PRT
<213> ORGANISM: Staphylococcus aureus

<400> SEQUENCE: 3

Ala Thr Ser Thr Lys Lys Leu His Lys Glu Pro Ala Thr Leu Ile Lys
            1               5                  10                 15

Ala Ile Asp Gly Asp Thr Val Lys Leu Met Tyr Lys Gly Gln Pro Met
                            20                  25                 30

Thr Phe Arg Leu Leu Leu Val Asp Thr Pro Glu Phe Asn Glu Lys Tyr
                            35                  40                 45

Gly Pro Glu Ala Ser Ala Phe Thr Lys Lys Met Val Glu Asn Ala Lys
                        50                  55                 60

Lys Ile Glu Val Glu Phe Asp Lys Gly Gln Arg Thr Asp Lys Tyr Gly
            65                  70                  75                 80

Arg Gly Leu Ala Tyr Ile Tyr Ala Asp Gly Lys Met Val Asn Glu Ala
                            85                  90                 95

Leu Val Arg Gln Gly Leu Ala Lys Val Ala Tyr Val Tyr Lys Gly Asn
                            100                 105                110

Asn Thr His Glu Gln Leu Leu Arg Lys Ala Glu Ala Gln Ala Lys Lys
                        115                 120                125

Glu Lys Leu Asn Ile Trp Ser Glu Asp Asn Ala Asp Ser Gly Gln
                130                 135                 140
```

INSERTION OF CHARGE IN THE HYDROPHOBIC INTERIOR OF PROTEINS AS A STRATEGY FOR ENGINEERING PH-SENSITIVE SWITCHES

CROSS-REFERENCE TO RELATED APPLICATIONS

This application claims the benefit of U.S. Provisional Application No. 61/887,099, filed Oct. 4, 2013, which is incorporated herein by reference in its entirety.

FEDERALLY SPONSORED RESEARCH OR DEVELOPMENT

This presently disclosed subject matter was made with government support under GM073838 awarded by the National Institutes of Health (NIH). The government has certain rights in the presently disclosed subject matter.

BACKGROUND

Protein folding is a highly cooperative process; therefore, folding landscapes are usually dominated by the fully folded and the unfolded states (Anfinsen, Science 181: 223-230 (1973); Rose et al., Proc. Natl. Acad. Sci. USA 103: 16623-16633 (2006)). In general, partially unfolded proteins are unstable relative to fully folded proteins and only transiently populated, if at all (Bai et al., Science 269: 192-197 (1995); Bouvignies et al., Nature 477: 111-114 (2011); Hansen et al. J. Biomol. NMR 41: 113-120 (2008); Westerheide and Morimoto, J. Biol. Chem. 280: 33097-33100 (2005); Dul et al., J. Cell Biol. 152: 705-716 (2001)). This suppression of folding intermediates minimizes the availability of aggregation-prone, partially folded species and ensures the success of the folding reaction (Westerheide and Morimoto, J. Biol. Chem. 280: 33097-33100 (2005); Dul et al., J. Cell Biol. 152: 705-716 (2001); Neudecker et al., Science 336: 362-366 (2012); Smith et al., J. Mol. Biol. 330: 943-954 (2003); Chiti et al., EMBO J. 19: 1441-1449 (2000)). Partially unfolded states are of great interest for the insight they contribute into the origins of folding cooperativity (Baldwin, Annu. Rev. Biophys. 37: 1-21 (2008)), folding mechanisms (Englander, Annu. Rev. Bioph. Biom. 29: 213-238 (2000); Sosnick and Barrick, Curr. Opin. Struc. Biol. 21: 12-24 (2011)), functional roles in energy transduction processes (Ihee. et al., Proc. Natl. Acad. Sci. USA 102: 7145-7150 (2005)), and the genesis and propagation of aggregation and misfolding diseases (Neudecker et al., Science 336: 362-366 (2012); Smith et al., J. Mol. Biol. 330: 943-954 (2003); Chiti et al., EMBO J. 19: 1441-1449 (2000)). Direct structural characterization of partially unfolded proteins is challenging because their equilibrium population is usually insignificant (Bouvignies et al., Nature 477: 111-114 (2011)).

Internal ionizable groups are relatively rare. Those that are present invariably play essential roles in energy transduction processes, usually involving $H^+$ or $e^-$ transfer reactions (Lanyi, BBA Bioenergetics 1757: 1012-1018 (2006); Pisliakov et al., Proc. Natl. Acad. Sci. USA 105: 7726-7731 (2008); Von Ballmoos et al., Annu. Rev. Biochem. 78: 649-672 (2009)). Internal groups usually titrate with anomalous $pK_a$ values because charged species are not compatible with the hydrophobic and dry interior of proteins.

Proteins capable of sensing and responding functionally to small changes in pH near physiological values are of significant biotechnological interest. The structural motif that acts as the pH sensor in naturally occurring pH switch proteins that undergo biologically essential pH-driven conformational transitions usually consists of His residues in interactions with polar or ionizable groups. However, engineering artificial pH sensing proteins by introduction of His residues is challenging. The presently disclosed subject matter is directed to methods for producing proteins comprising artificial pH-sensitive conformational switches within internal regions of the proteins.

SUMMARY

In one aspect, the presently disclosed subject matter provides a method for engineering a non-naturally occurring protein comprising an artificial pH-sensitive conformational switch that responds to a change in pH by causing a global unfolding of the protein, the method comprising the steps of: (a) identifying one or more amino acid residues within an internal region, particularly a hydrophobic interior region, of the protein; and (b) substituting one or more of the amino acid residues within the internal region of the protein with one or more ionizable amino acid residues, wherein the one or more ionizable amino acid residues titrate with a $pK_a$ value shifted relative to the normal $pK_a$ value in water for the one or more ionizable amino acid residues; thereby engineering the non-naturally occurring protein comprising an artificial pH-sensitive conformational switch that responds to a change in pH by causing a global unfolding of the protein. In particular aspects of the presently disclosed subject matter, the methods produce a protein comprising an artificial pH-sensitive conformational switch that unfolds within a range of pH from about 5.0 pH to about 9.0 pH, particularly from about 6.0 pH to about 8.0 pH, more particularly from about 6.5 pH to about 7.5 pH, and even more particularly within a physiological pH range. In another particular aspect of the presently disclosed subject matter, the one or more ionizable amino acid residues that titrate with a $pK_a$ value shifted relative to the normal $pK_a$ value in water for the one or more ionizable amino acid residues are selected from the group consisting of Lys, Asp, and Glu.

In another aspect, the presently disclosed subject matter provides a protein produced by any of the methods described herein. In particular, the presently disclosed subject matter provides a non-naturally occurring protein comprising an artificial pH-sensitive conformational switch that responds to a change in pH by causing a global unfolding of the protein, wherein the one or more ionizable amino acid residues titrate with a $pK_a$ value shifted relative to the normal $pK_a$ value in water for the one or more ionizable amino acid residues. In a particular aspect, the one or more ionizable amino acid residues have been substituted for one or more amino acid residues in the internal region of the protein. In another particular aspect of the presently disclosed subject matter, the protein comprising the artificial pH-sensitive conformational switch unfolds within a range of pH from about 5.0 pH to about 9.0 pH, particularly from about 6.0 pH to about 8.0 pH, more particularly from about 6.5 pH to about 7.5 pH, and even more particularly within a physiological pH range. In a further particular aspect of the presently disclosed subject matter, the one or more ionizable amino acid residues that titrate with a $pK_a$ value shifted relative to the normal $pK_a$ value in water for the one or more ionizable amino acid residues are selected from the group consisting of Lys, Asp, and Glu.

Certain aspects of the presently disclosed subject matter having been stated hereinabove, which are addressed in

BRIEF DESCRIPTION OF THE FIGURES

Figure 1A:
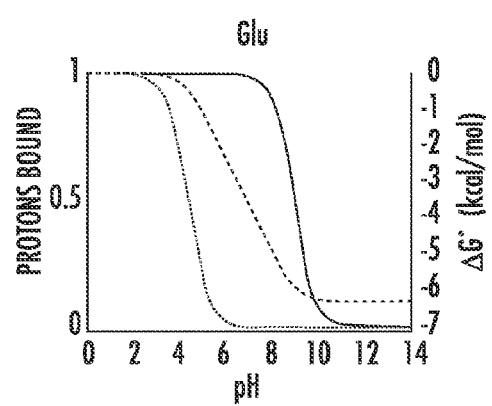
Figure 1B:
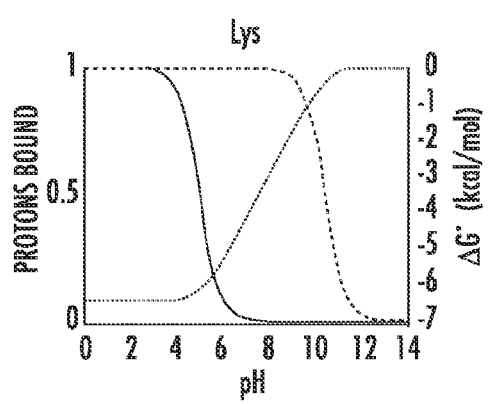
Figure 2:
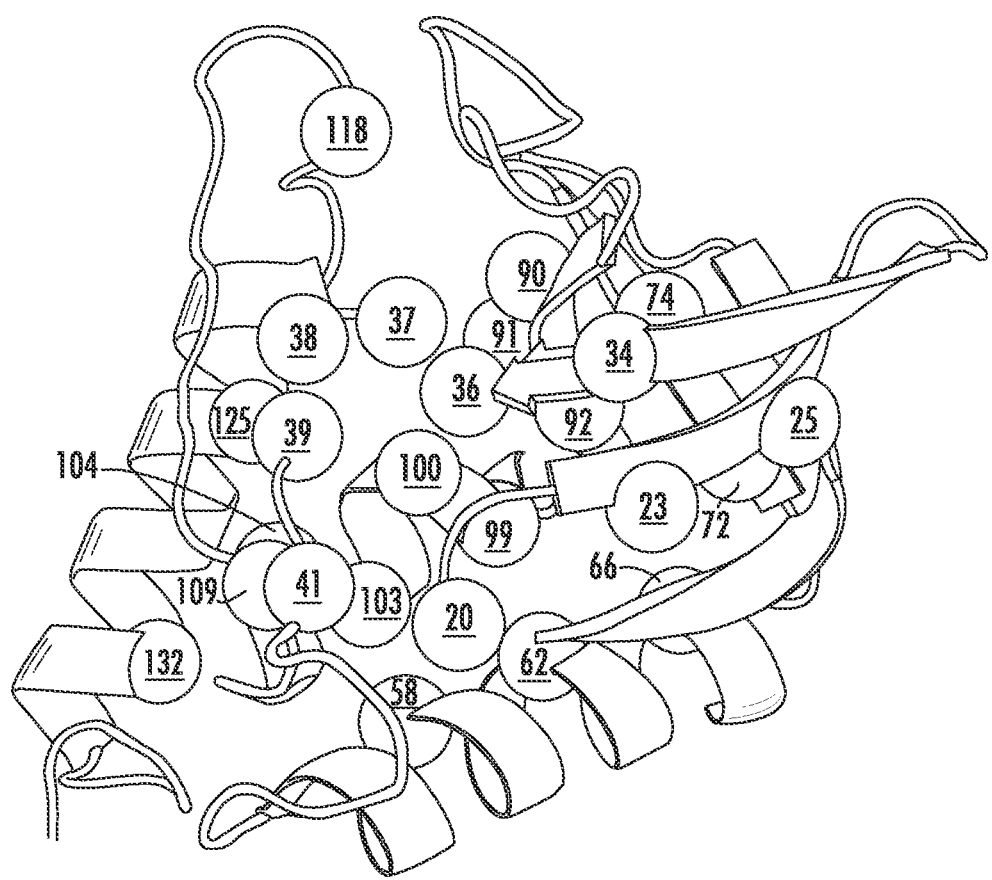
Figure 3:
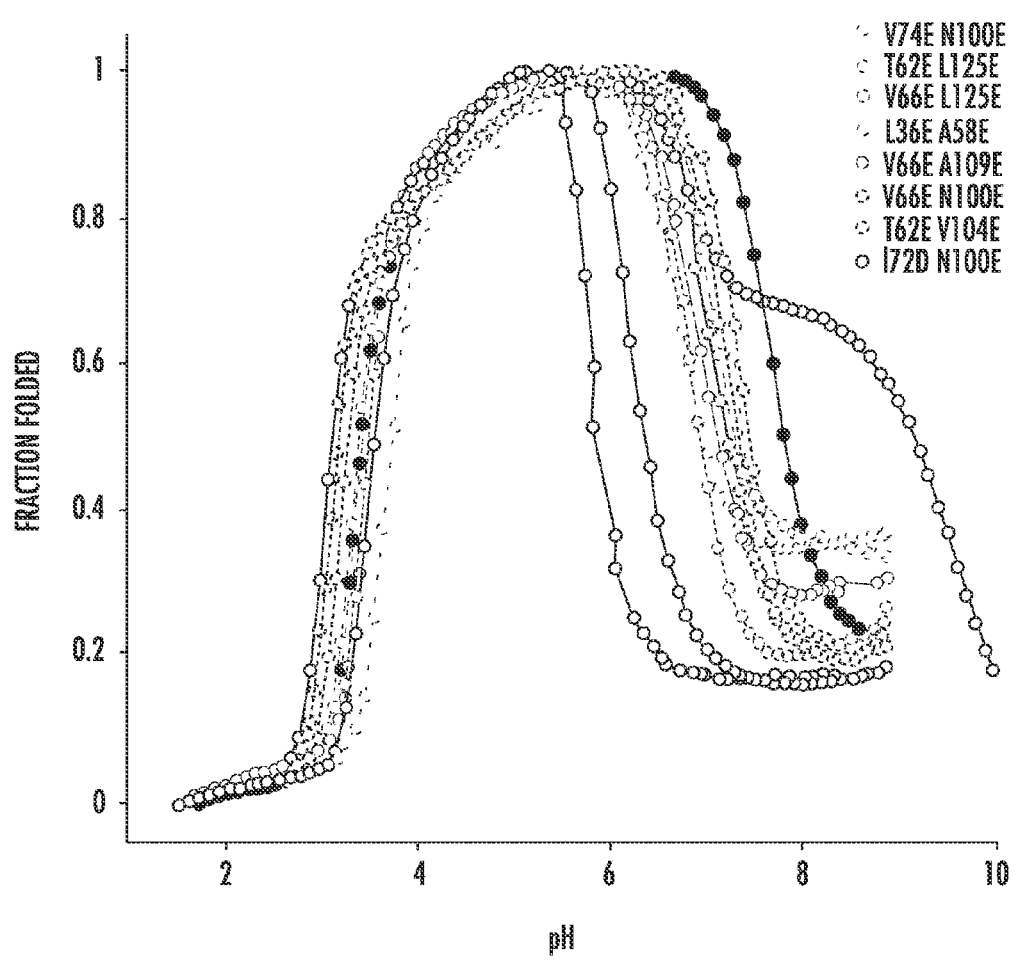
Figure 4:
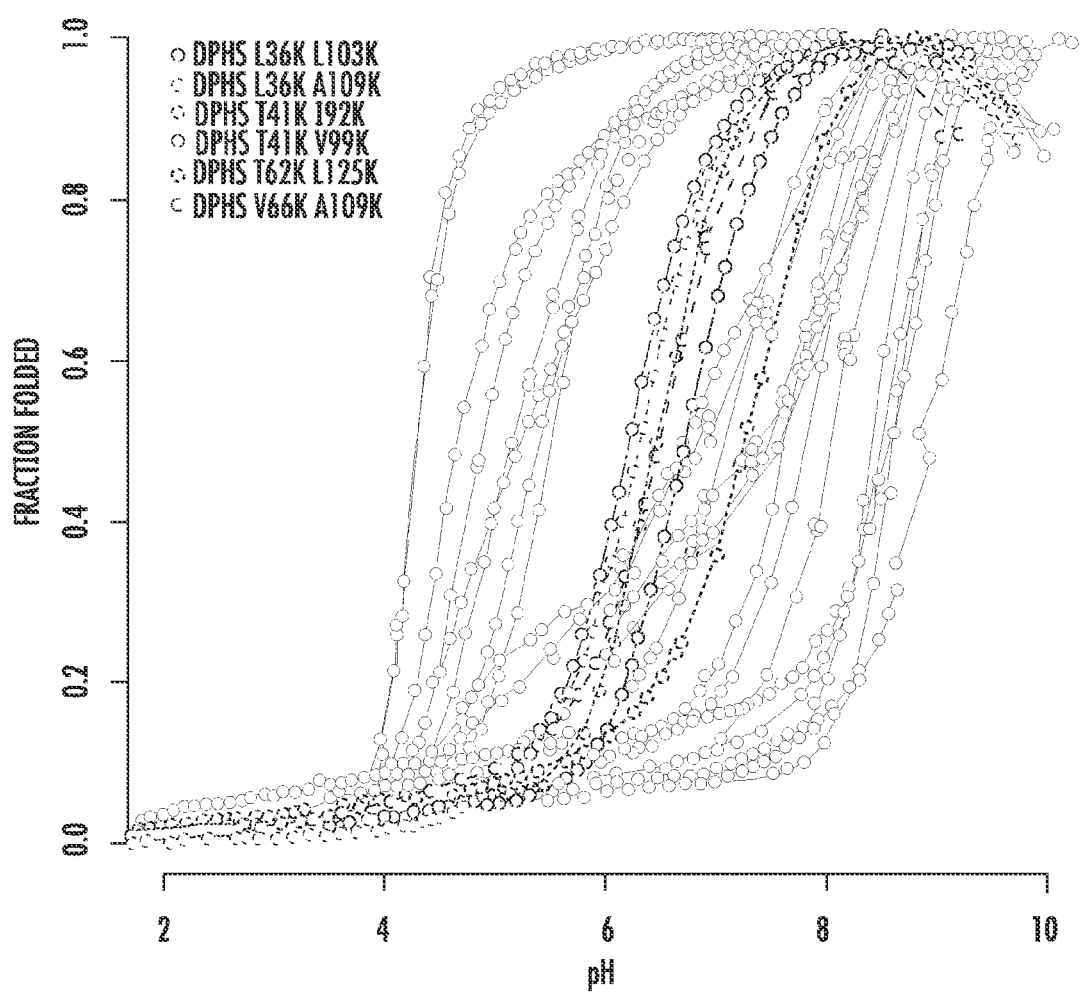
Figure 5:
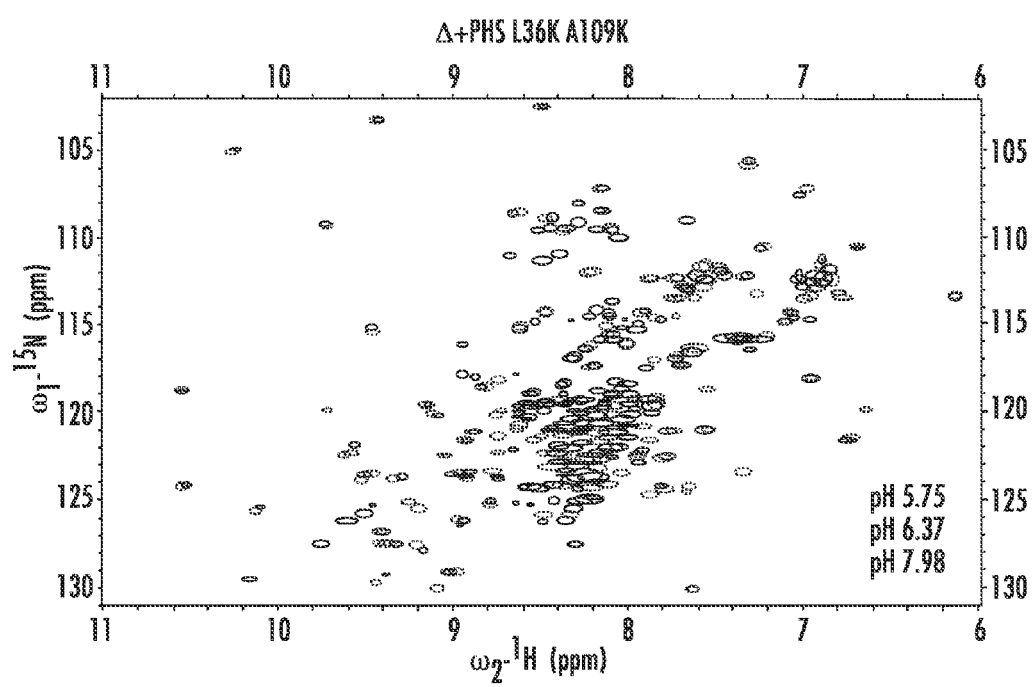
Figure 6:
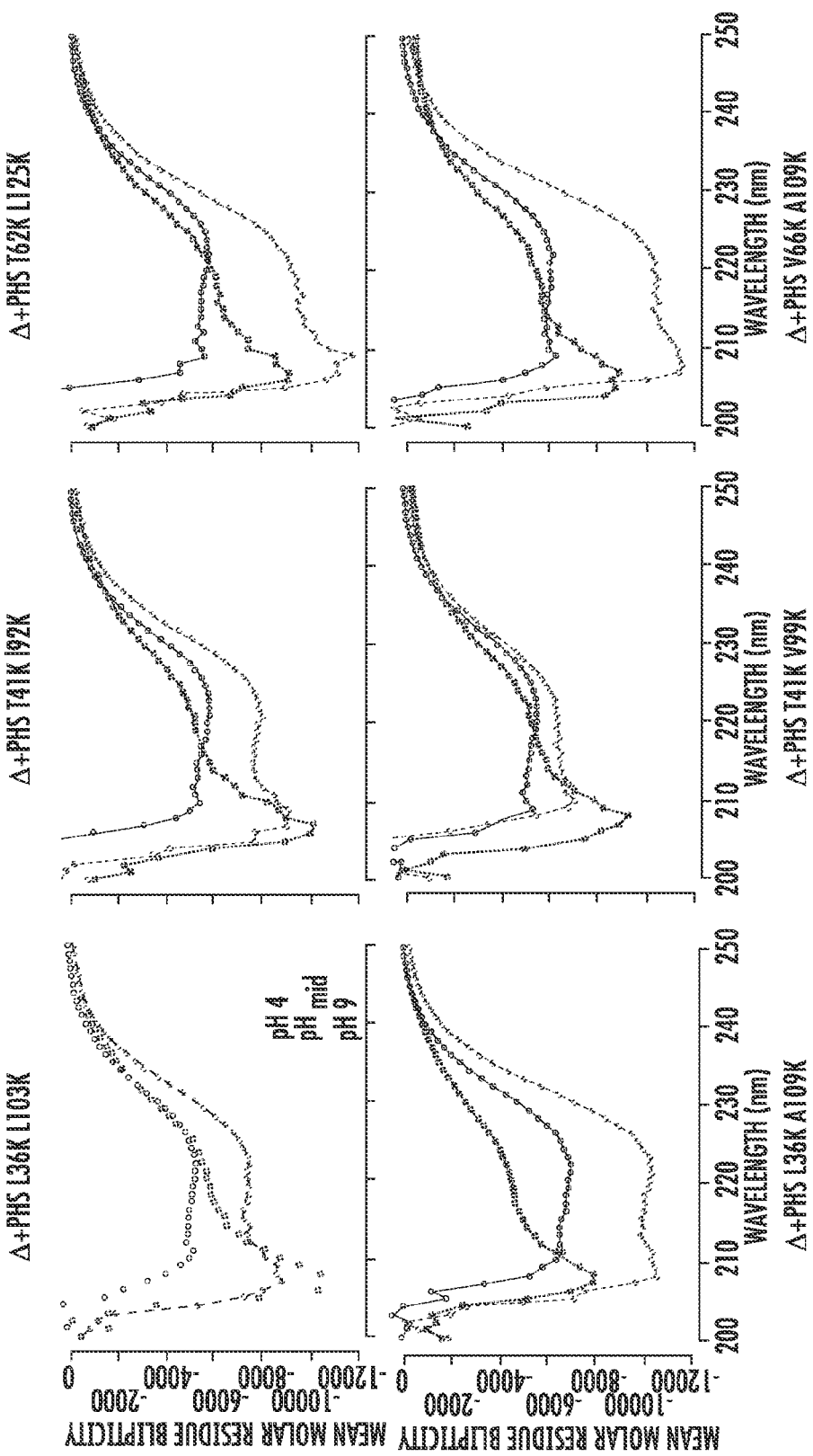
Figure 7:
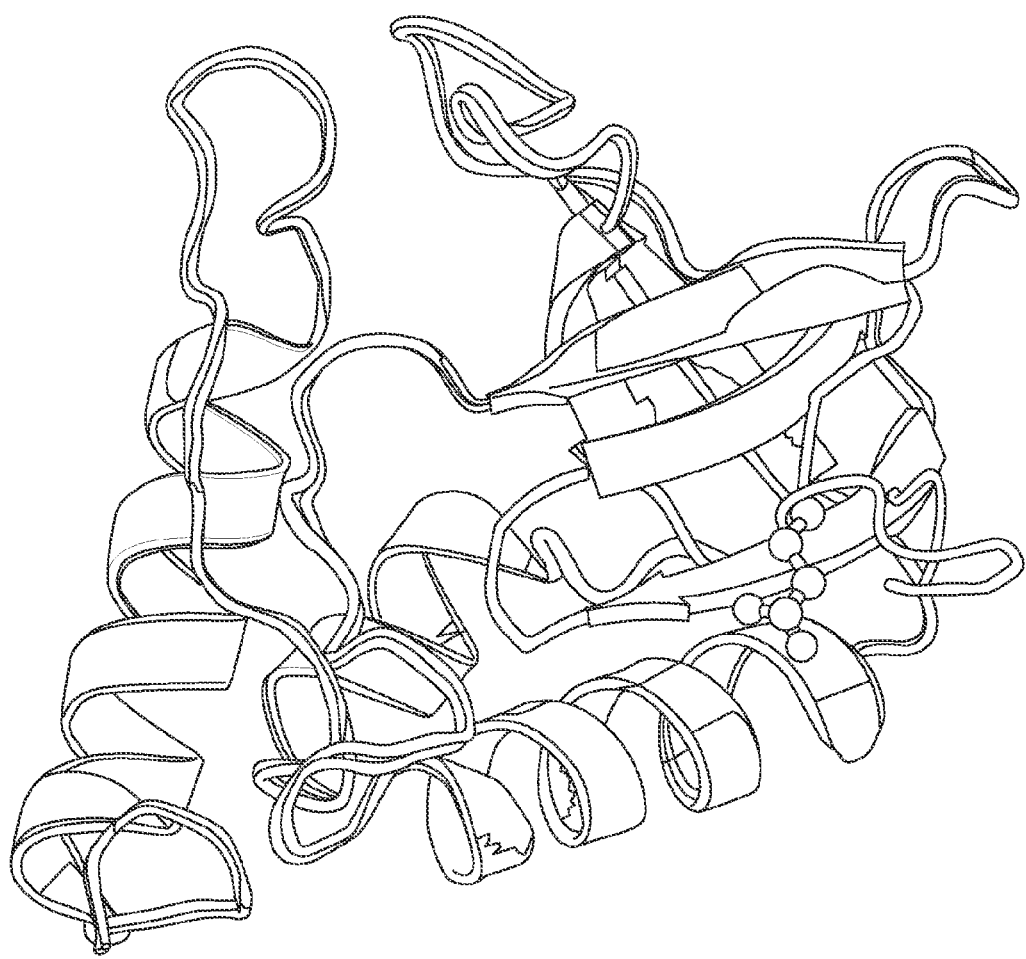
Figure 8A:
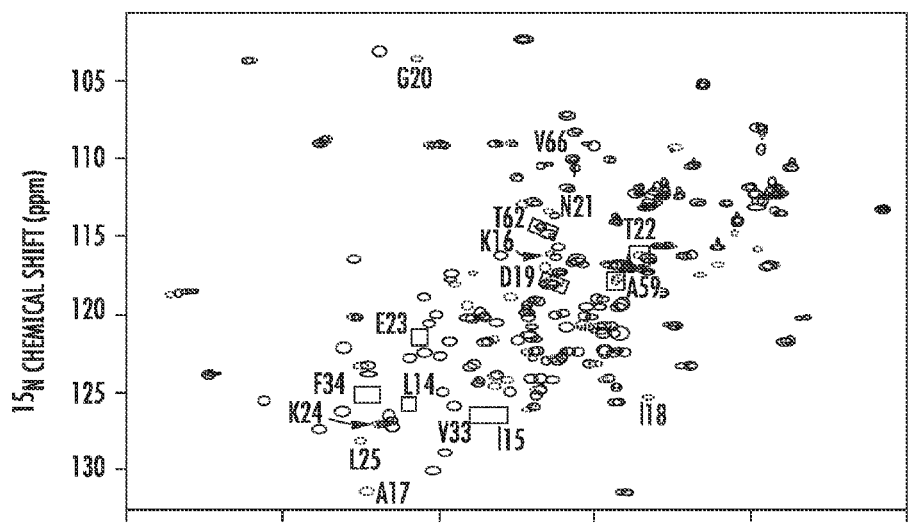
Figure 8B:
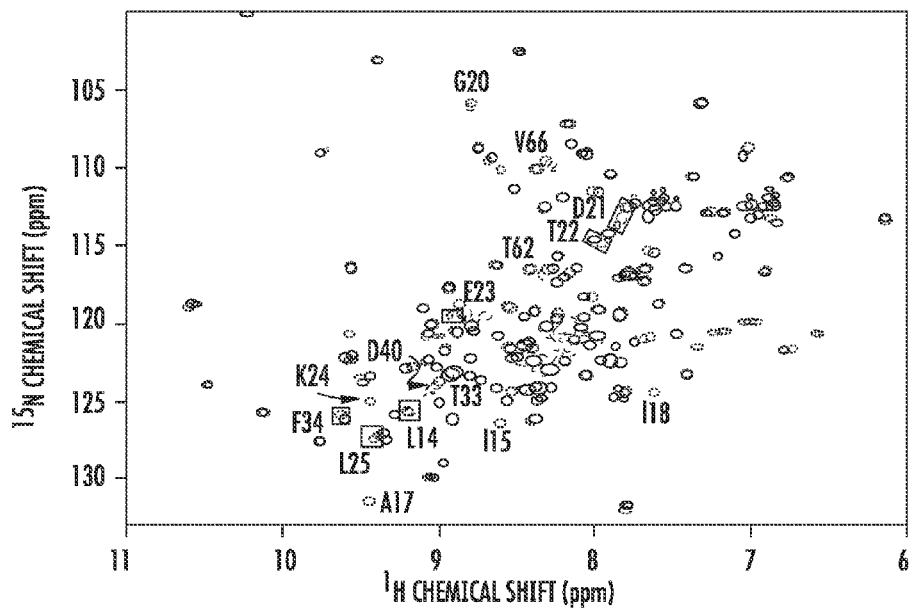
Figure 9:
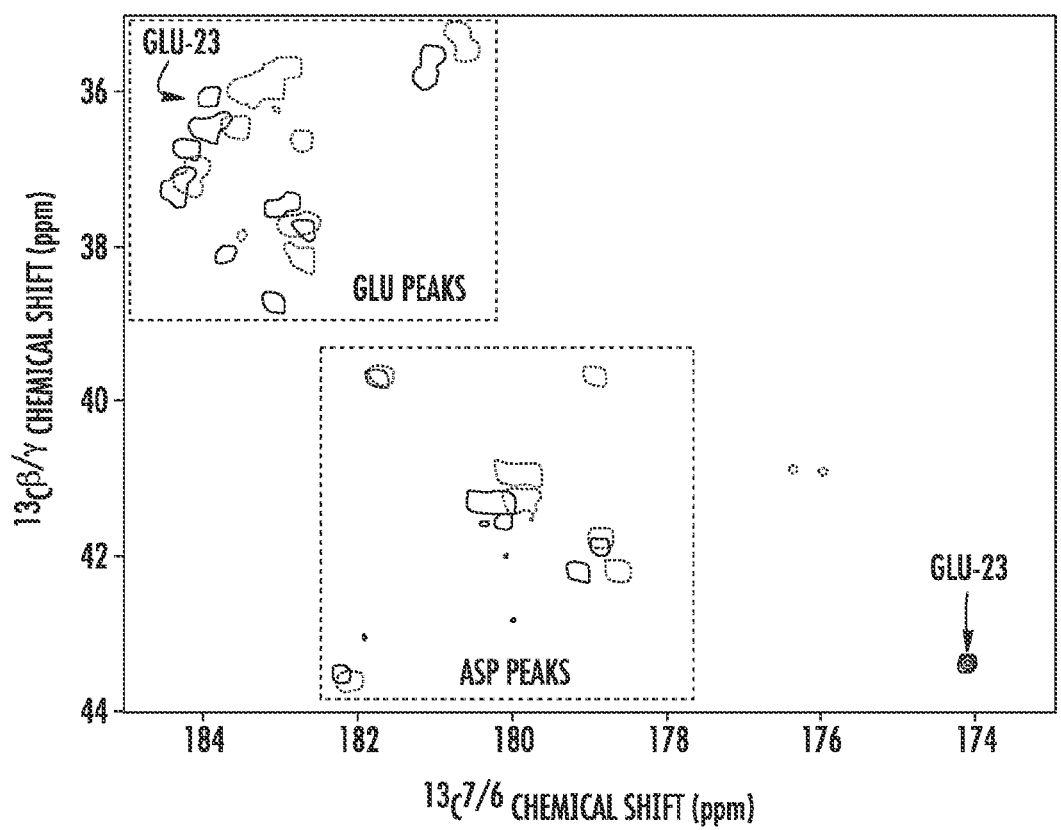
Figure 10:
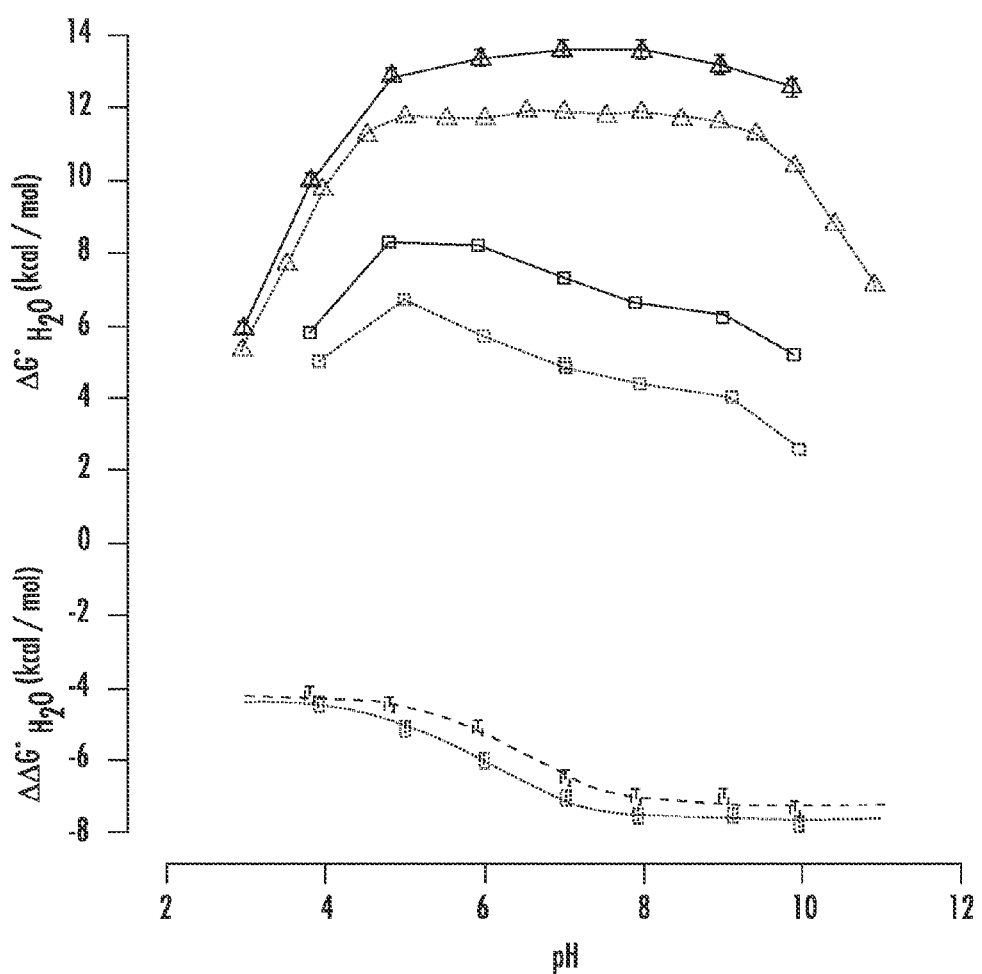
Figure 11A:
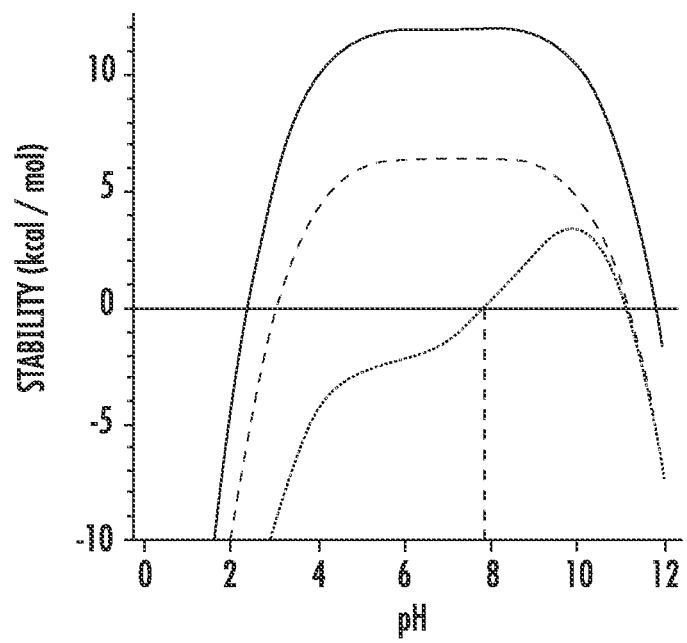
Figure 11B:
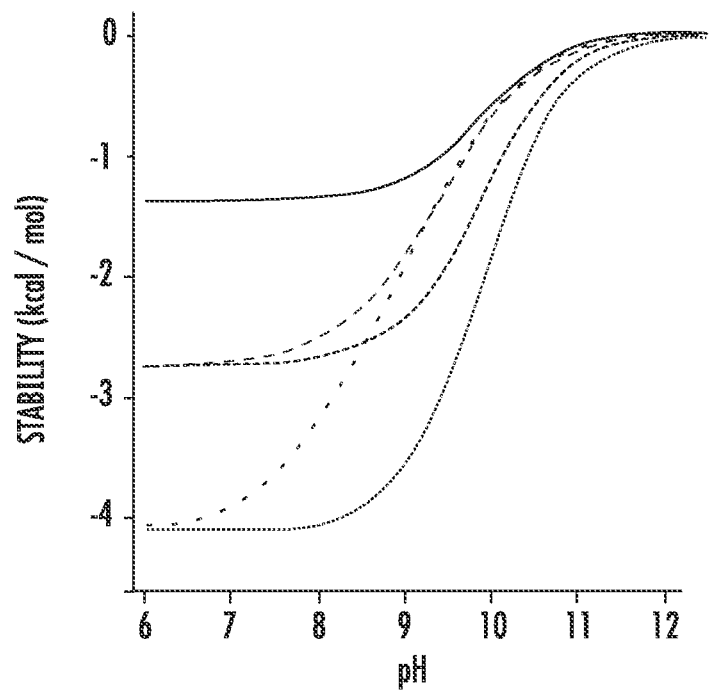
Figure 12A:
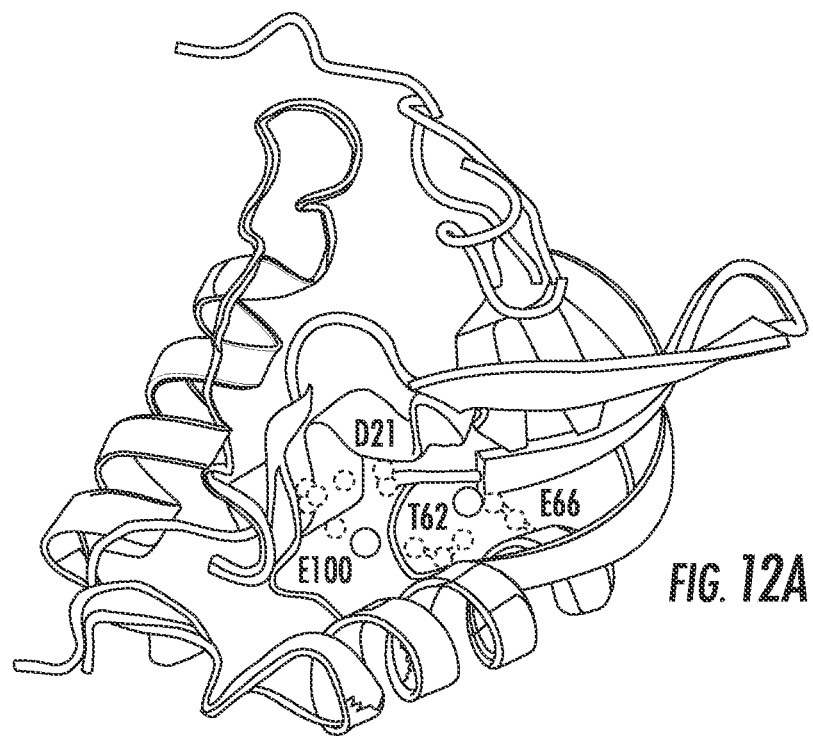
Figure 12B:
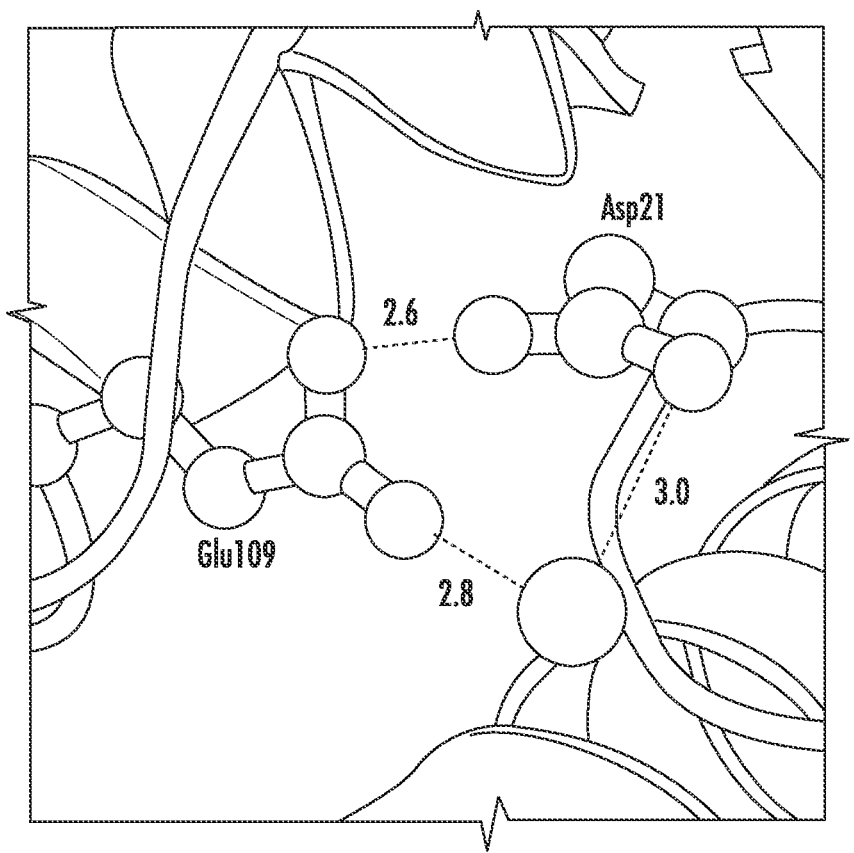
Figure 13A:
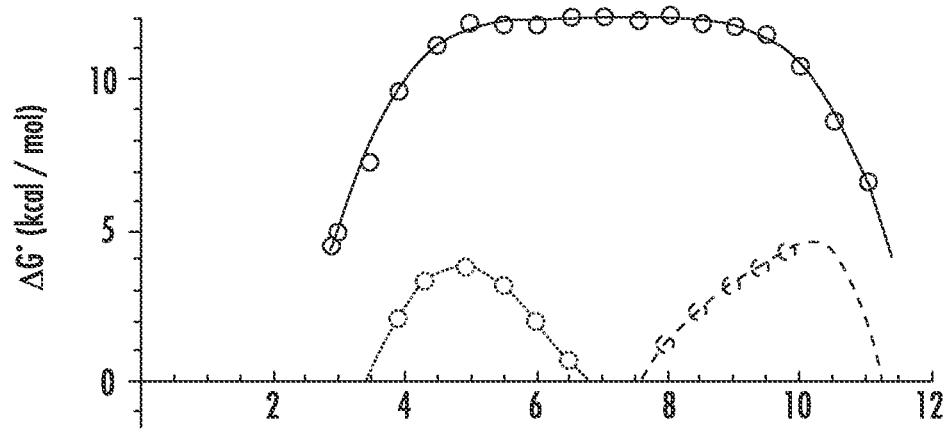
Figure 13B:
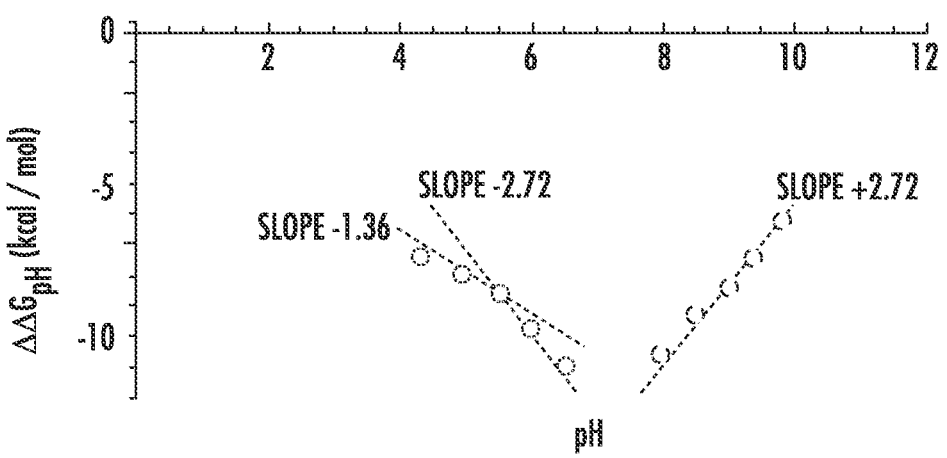
Figure 14A:
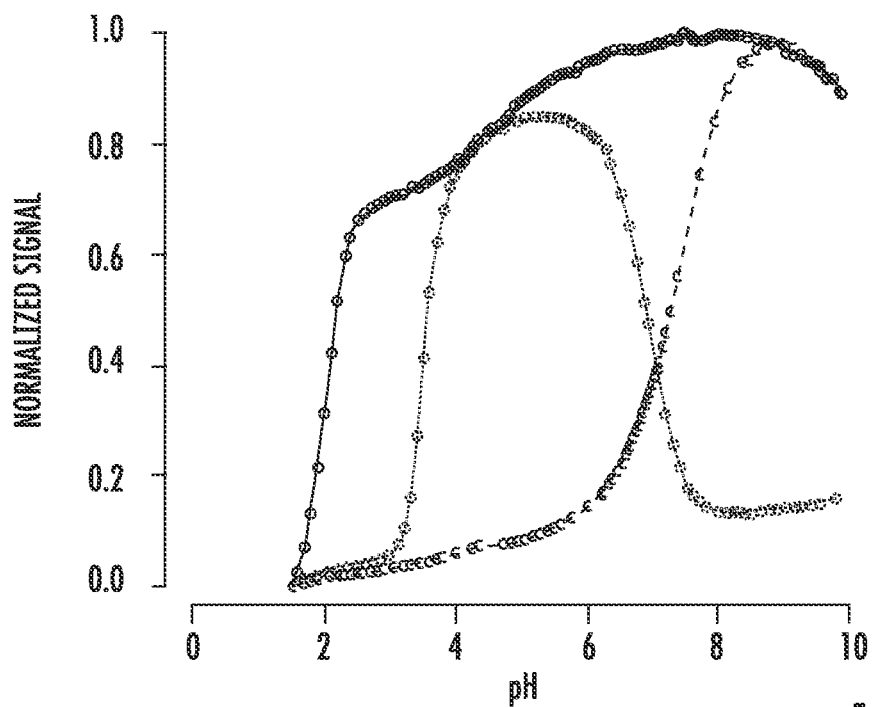
Figure 14B:
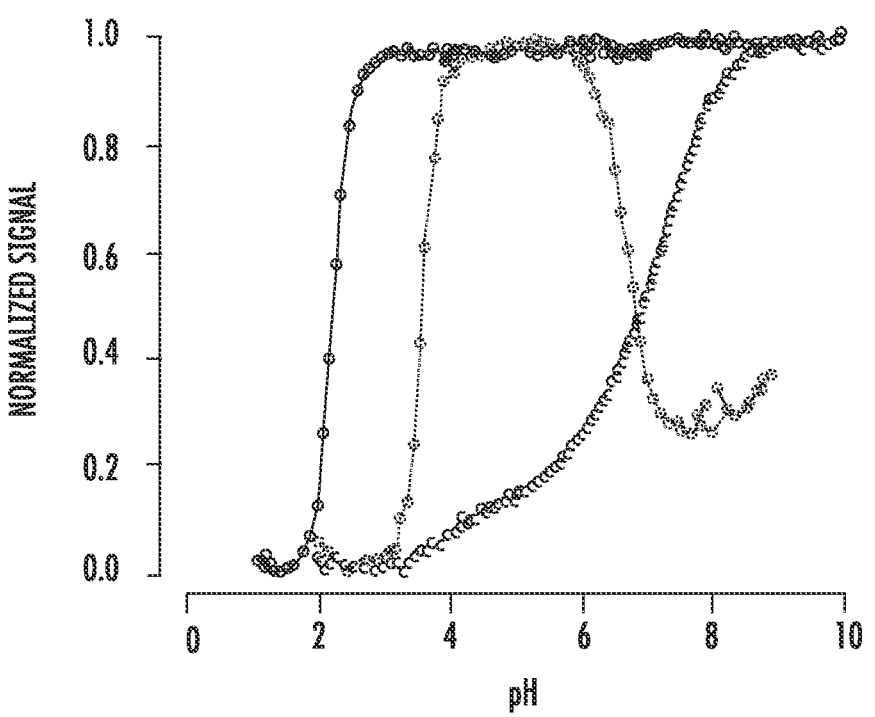
Figure 15A:
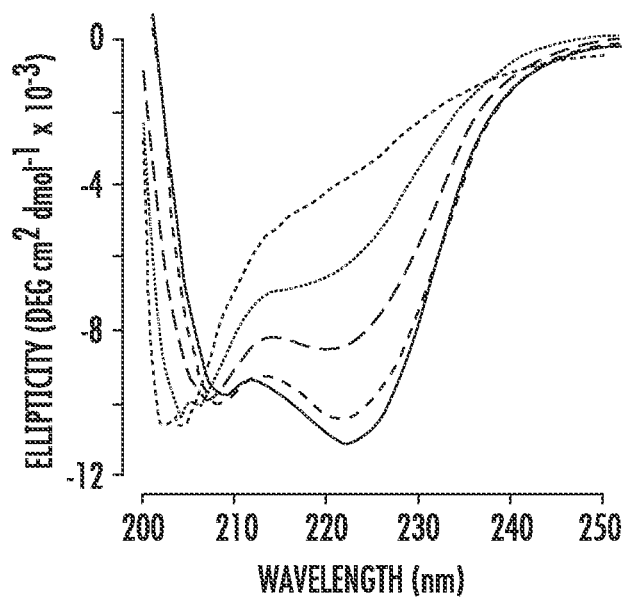
Figure 15B:
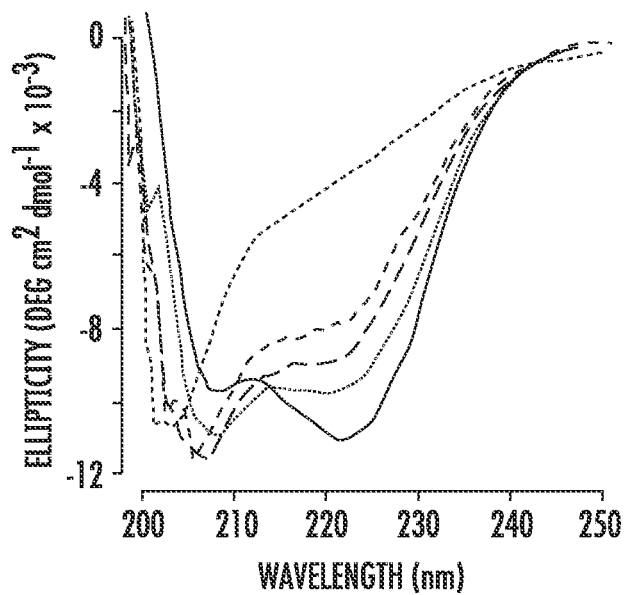
Figure 16A:
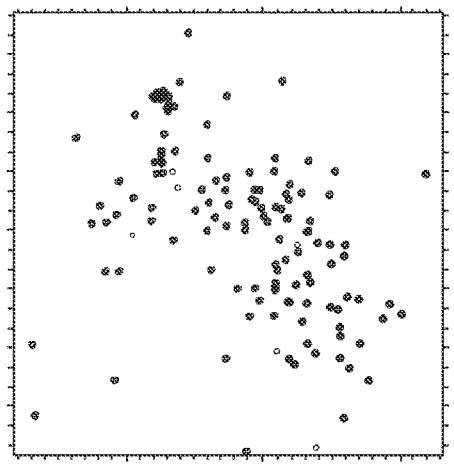
Figure 16B:
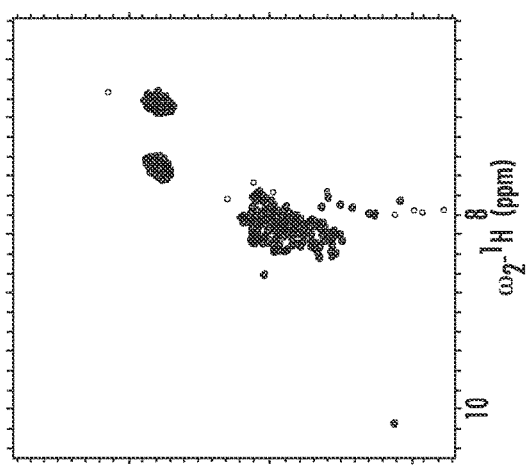
Figure 16C:
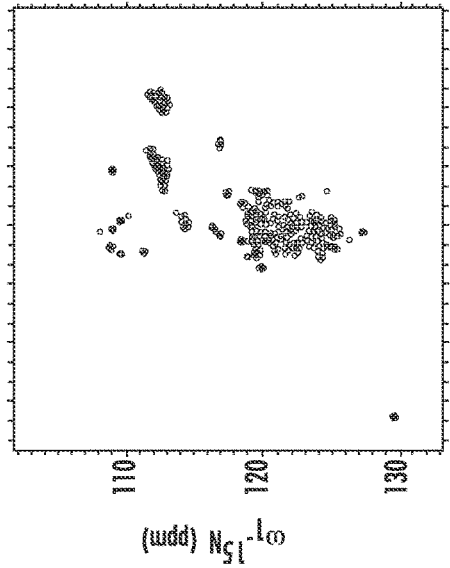
Figure 16D:
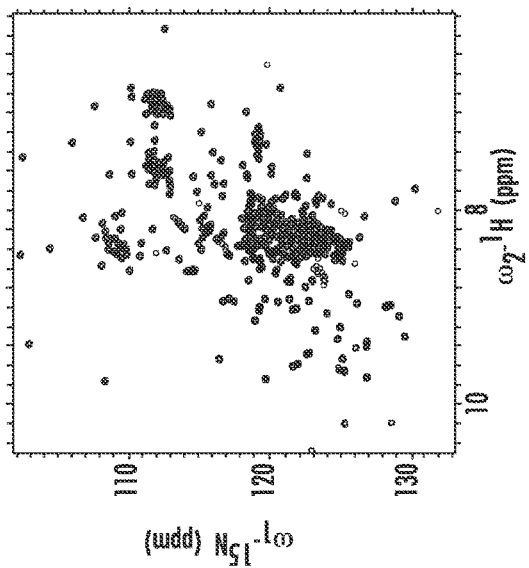

Having thus described the presently disclosed subject matter in general terms, reference will now be made to the accompanying Drawings, which are not necessarily drawn to scale, and wherein:

FIGS. 1A-1B show that ionizable groups with anomalous $pK_a$ values affect the pH dependence of global stability ($\Delta G°$): A) glutamic acid (Glu); and B) lysine (Lys);

FIG. 2 shows the 25 internal locations in staphylococcal nuclease selected for substitution with ionizable groups;

FIG. 3 shows acid titrations monitored with tryptophan fluorescence using staphylococcal nuclease with substituted glutamic acid residues;

FIG. 4 shows acid titrations monitored with tryptophan fluorescence using staphylococcal nuclease with substituted lysine residues;

FIG. 5 shows $^1H$-$^{15}N$ HSQC spectra monitored as a function of pH for the the Δ+PHS L36K A109K variant;

FIG. 6 shows Far-UV CD measurements for Δ+PHS L36K L103K, Δ+PHS T41K A192K, Δ+PHS T62K L125K, Δ+PHS L36K A109K, Δ+PHS T41K V99K, and Δ+PHS V66K A109K;

FIG. 7 shows the structure of Δ+NVIAGLA/V23E at pH 8 (blue, PDB entry 3TME), superimposed on the structure of the Δ+PHS/V23E variant at pH 6 (grey, PDB entry 3QOL). One of two conformations of the Glu-23 side chain in Δ+NVIAGLA/V23E is shown in ball-and-stick representation for both variants. Residues that are present in $^1H$-$^{15}N$ HSQC spectra at low pH, but broadened or totally absent at pH greater than 6.6 at 25° C., are shown in green;

FIGS. 8A-8B show $^1HN$-$^{15}N$ HSQC spectra recorded for the Δ+NVIAGLA/V23E (A) and Δ+PHS/V23E (B) variants of staphylococcal nuclease (SNase) at 100 mM KCl and 25° C. Spectra were recorded at pH 5.7 (red), 6.6 (green) and 7.6 (blue) for the Δ+NVIAGLA/V23E variant. Fifteen residues (15-24, 33-34, 59, 62 and 66, labeled above) displayed line broadening between pH 5.7 and 7.6, which is not observed in the Δ+NVIAGLA protein used as reference. Spectra were recorded at pH 6.3 (red), 6.6 (orange), 6.9 (green) and 7.3 (blue) for the Δ+PHS/V23E variant;

FIG. 9 shows Asp/Glu selective, Asn/Gln suppressed, CBCGCO spectra recorded on a 700 μM $^{15}N/^{13}C$-labeled V23E variant of Δ+NVIAGLA SNase at pH 5.0 (red) and pH 8.5 (blue). The typical chemical shift ranges for Asp $C^{\beta/\gamma}$-$C^{\gamma/\delta}$ and Glu $C^{\beta/\gamma}$-$C^{\gamma/\delta}$ cross peaks are highlighted by boxes. The resonances of Glu-23 at both pH values are indicated by an arrow with the same color scheme as above. The Glu-23 cross peak at pH 5.0 was folded into the spectrum in the indirect dimension; the aliased chemical shift of $C^{\beta/\gamma}$ is 31.4 ppm. The spectra were collected with a Bruker 600-MHz spectrophotometer equipped with a TCI cryogenic probe with a cryocooled $^{13}C$ preamplifier. Spectra were collected with 64 scans per FID at 25° C. at each pH and required approximately 2 hours to acquire;

FIG. 10 shows measurement of the $pK_a$ value of Glu-23 in the Δ+PHS/V23E (red) and Δ+NVIAGLA/V23E (black) variants of SNase though linkage analysis of the pH dependence of thermodynamic stability. The thermodynamic stability ($\Delta G°$ $H_2O$) of the reference proteins Δ+NVIAGLA and Δ+PHS (triangles) and the V23E variants thereof (squares) as measured by GdnHCl denaturation monitored by Trp fluorescence. The error in the measurements is on the order of the size of the symbols. The solid lines are meant only to guide the eye. The difference in thermodynamic stability of V23E variants and the reference proteins (variant—reference) (circles). The short-dashed line describes the fit to equation 1 for a single group to the data (Dwyer et al., Biophys. J. 79: 1610-1620 (2000); García-Moreno et al., Biophys. Chem. 64: 211-224 (1997));

FIGS. 11A-11B show simulations of the effects of buried ionizable residues with anomalous $pK_a$ values on the pH sensitivity of stability of proteins. This case represents a protein with internal Lys residues: (A) pH dependence of stability of the background protein, the Δ+PHS variant of SNase (black). Variant in which the buried Lys has a normal $pK_a$ of 10.4 (blue) and an anomalous $pK_a$ of 6 (red); and (B) consequences of the insertion of internal Lys residues) on the stability of a protein relative to stability at high pH. Case of single Lys with a $pK_a$ shift of 1, 2, or 3 pH units (solid black, blue, red lines, respectively) and 2 or 3 Lys with $pK_a$ shift of 2 pH units (dashed black, dotted black, respectively);

FIGS. 12A-12B show the crystal structure of the Δ+PHS/V66E/A109E variant: (A) overlay of the structures of Δ+PHS (gray) with the Δ+PHS/V66E/A109E variant (gold). Internal Glu side chains (E66 and E109) are shown, as well as side chains that coordinate the internal Glu residues. Places where there were large differences in the conformation of the backbone are highlighted in cyan. Crystallographic waters that coordinate internal Glu residues are represented in blue; and (B) microenvironment of the Glu-109 side chain showing close proximity to surface group Asp-21, and coordination of crystallographic water molecule, represented in blue;

FIGS. 13A-13B show: (A) pH dependence of thermodynamic stability ($\Delta G°_{H2O}$) of Δ+PHS variant of nuclease (black) Δ+PHS/T62K/L125K (red) and Δ+PHS/V66E/A109E (blue). Solid lines are meant only to guide the eye; and (B) difference in stability, calculated as $\Delta\Delta G° = \Delta G°$ (variant)—$\Delta G°$ (Δ+PHS). Dashed lines representing ideal behavior from the titration of 1 or 2 titrating ionizable groups, with slopes of 1.36 or 2.72, respectively;

FIGS. 14A-14B show acid titrations monitored by: (A) trp fluorescence; and (B) CD at 222 nm for Δ+PHS (black), Δ+PHS/V66E/A109E (red), and Δ+PHS/T62K/L125K (blue). Data have been normalized relative to the Δ+PHS curves;

FIGS. 15A-15B show far UV wavelength scans for (A) Δ+PHS/T62K/L125K and (B) Δ+PHS/V66E/A109E, at pH 5 (red), 9 (blue), and 7.5 or 7 (brown) for (A) and (B), respectively. Black curves are representative of folded (solid) and unfolded (dashed) SNase; and FIGS. 16A-16D show HSQC spectra of Δ+PHS/T62K/L125K at pH 6.49 (A) and pH 8.53 (B); and Δ+PHS/V66E/A109E at pH 5.09 (C) and pH 7.94 (D).

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

Many proteins interpret small changes in pH as physiological signals. For example, in many disease states, pH homeostasis is affected, such as in cancer where tumors are more acidic than normal tissue. Accordingly, the ability to modify proteins to engineer artificial pH sensing domains that could respond to small pH changes with a conformational change is useful for diagnostic and treatment purposes. However, naturally occurring pH sensitive switches would be very difficult to engineer because they depend on small effects arising from many surface ionizable residues.

The presently disclosed subject matter is directed to the surprising discovery that the introduction of ionizable amino acid residues that titrate with a $pK_a$ value shifted relative to the normal $pK_a$ value in water for the one or more ionizable amino acid residues in an internal region of a protein, particularly the hydrophobic interior of a protein, is effective for engineering an artificial pH-sensing domain in a protein that responds to a change in pH by causing a global unfolding of the protein. In some embodiments, the presently disclosed subject matter provides methods to modify proteins so they unfold cooperatively over a very narrow range of pH (e.g., centered around pH 7), particularly wherein the one or more ionizable amino acid residues that titrate with a $pK_a$ value shifted relative to the normal $pK_a$ value in water for the one or more ionizable amino acid residues are selected from the group consisting of Lys, Asp, and Glu.

I. Methods For Producing A Protein Comprising An Artificial Ph-Sensitive Conformational Switch In one embodiment, the presently disclosed subject matter provides a method for engineering a non-naturally occurring protein comprising an artificial pH-sensitive conformational switch that responds to a change in pH by causing a global unfolding of the protein, the method comprising the steps of: (a) identifying one or more amino acid residues within an internal region, particularly a hydrophobic interior region, of the protein; and (b) substituting one or more of the amino acid residues within the internal region of the protein with one or more ionizable amino acid residues, wherein the one or more ionizable amino acid residues titrate with a $pK_a$ value shifted relative to the normal $pK_a$ value in water for the one or more ionizable amino acid residues; thereby engineering the non-naturally occurring protein comprising an artificial pH-sensitive conformational switch that responds to a change in pH by causing a global unfolding of the protein. In particular aspects of the presently disclosed subject matter, the protein comprising the artificial pH-sensitive conformational switch unfolds within a range of pH from about 5.0 pH to about 9.0 pH, particularly from about 6.0 pH to about 8.0 pH, more particularly from about 6.5 pH to about 7.5 pH, and even more particularly within a physiological pH range. In another particular aspect of the presently disclosed subject matter, the one or more ionizable amino acid residues having anomalous $pK_a$ values as compared to the normal $pK_a$ values of each of the amino acid residues in water are selected from the group consisting of Lys, Asp, and Glu.

A. Protein Conformation, $pK_a$, and pH

Under physiological conditions, proteins (polymer chains of peptide-linked amino acids) normally do not exist as extended linear polymer chains. A combination of molecular forces, including hydrogen bonding, hydrophilic and hydrophobic interactions, promote thermodynamically more stable secondary structures that can be highly organized (helices, beta pleated sheets, etc.). These structures can combine to form higher order structures with critical biological functions. Natural proteins are peptide-linked polymers containing 20 different amino acids, each with a different side-chain. The details of the folding into higher order structures are dependent on the type, frequency and primary sequence of the amino acids in the protein. Since each position in the polymer chain can be occupied by 20 different amino acids, the thermodynamic rules that describe the details of protein folding can be complex. For example, it is not yet possible to design a synthetic protein with a substrate-specific enzymatic site that is predicted by the primary amino acid sequence. More complete discussions of the structure and function of proteins are found in Dickerson et al. "The Structure and Action of Proteins" Harper and Row, New York, 1970 and Lehninger "Biochemistry" Worth, New York, pp. 109-146 (1970).

Some basic rules of protein folding have been discovered. In general, the side chains of the 20 L-amino acids commonly found in natural proteins can be placed in two categories: hydrophobic/non-polar and hydrophilic/polar, each playing separate roles in protein conformation. In the standard "oil drop" model for protein folding, the amino acids with more hydrophobic side chains (Val, Leu, Phe, Met, He) are sequestered to the inside of the protein structure, away from the aqueous environment. Frequently, these hydrophobic side chains form "pockets" that bind molecules of biological significance. On the other hand, hydrophilic amino acids (e.g. Lys, Arg, Asp, Glu) are most frequently distributed on the outer surface of natural proteins, providing overall protein solubility and establishing a superstructure for the internalized hydrophobic domains. Internal polar and ionizable groups are essential for enzymatic catalysis, proton transport, redox reactions, and many other functional properties of proteins. To engineer novel enzymes or to modify the function of existing ones, and to build switches that can be used to modify the stability of proteins in response to changes in pH, it is necessary to introduce polar or ionizable groups or to modify the properties of existing ones in the protein's interior region. Internal polar and ionizable amino acid groups however, usually destabilize proteins.

In computational biology, protein $pK_a$ calculations are used to estimate the $pK_a$ values of amino acids as they exist within proteins. These calculations complement the $pK_a$ values reported for amino acids in their free state, and are used frequently within the fields of molecular modeling, structural bioinformatics, and computational biology. $pK_a$ values of amino acid side chains play an important role in defining the pH-dependent characteristics of a protein. The pH-dependence of the activity displayed by enzymes and the pH-dependence of protein stability, for example, are properties that are determined by the $pK_a$ values of amino acid side chains. The $pK_a$ values of an amino acid side chain in solution is typically inferred from the $pK_a$ values of model compounds (i.e. compounds that are similar to the side chains of amino acids).

When a protein folds, the titratable amino acids in the protein are transferred from a solution-like environment to an environment determined by the 3-dimensional structure of the protein. For example, in an unfolded protein an aspartic acid typically is in an environment which exposes the titratable side chain to water. When the protein folds the aspartic acid may be buried deep in the protein interior with no exposure to solvent. In the folded protein the aspartic acid will be closer to other titratable groups in the protein and will also interact with permanent charges (e.g. ions) and dipoles in the protein. All of these effects alter the $pK_a$ value of the amino acid side chain, and p a calculation methods generally calculate the effect of the protein environment on the model $pK_a$ value of an amino acid side chain. Typically the effects of the protein environment on the amino acid $pK_a$ value are divided into pH-independent effects and pH-dependent effects. The pH-independent effects (desolvation, interactions with permanent charges and dipoles) are added to the model $pK_a$ value to give the intrinsic $pK_a$ value. The pH-dependent effects cannot be added in the same straightforward way and have to be accounted for using Boltzmann summation, Tanford-Roxby iterations or other methods.

The interplay of the intrinsic $pK_a$ values of a system with the electrostatic interaction energies between titratable groups can produce quite spectacular effects such as non-Henderson-Hasselbalch titration curves and even back-titration effects. $pK_a$ Tool provides an easy interactive and instructive way of modifying and observing these effects. Several software packages and webserver are available for the calculation of protein $pK_a$ values. Some methods are based on solutions to the Poisson-Boltzmann equation (PBE), often referred to as FDPB-based methods (FDPB is for "finite difference Poisson-Boltzmann"). The PBE is a modification of Poisson's equation that incorporates a description of the effect of solvent ions on the electrostatic field around a molecule. The H++ web server, the pKD webserver, MCCE and Karlsberg+ use the FDPB method to compute $pK_a$ values of amino acid side chains. FDPB-based methods calculate the change in the p a value of an amino acid side chain when that side chain is moved from a hypothetical fully solvated state to its position in the protein. To perform such a calculation, one needs theoretical methods that can calculate the effect of the protein interior on a $pK_a$ value, and knowledge of the $pK_a$ values of amino acid side chains in their fully solvated states. A set of empirical rules relating the protein structure to the $pK_a$ values of ionizable residues have been developed by Li, Robertson, and Jensen (Li et al. Proteins Struct. Funct. Bioinf. 61(4): 704-721 (2005)). These rules form the basis for the web-accessible program called $PROPK_A$ for rapid predictions of $pK_a$ values.

The pH value where the titratable group is half-protonated is equal to the $pK_a$ if the titration curve follows the Henderson-Hasselbalch equation. Most $pK_a$ calculation methods assume that all titration curves are Henderson-Hasselbalch shaped, and $pK_a$ values in $pK_a$ calculation programs are therefore often determined in this way. Some software developed for protein $pK_a$ calculations include: Accelrys$PK_A$ Accelrys CHARMm based $pK_a$ calculation; H++Poisson-Boltzmann based $pK_a$ calculations; MCCE Multi-Conformation Continuum Electrostatics; Karlsberg+ $pK_a$ computation with multiple pH adapted conformations; pKD server $pK_{a\ a}$ calculations and $pK_a$ value re-design; and $PROPK_A$ Empirical calculation of $pK_a$ values.

As stated above, in one embodiment, the presently disclosed subject matter provides a method for engineering a non-naturally occurring protein comprising an artificial pH-sensitive conformational switch that responds to a change in pH by causing a global unfolding of the protein, the method comprising the steps of: (a) identifying one or more amino acid residues within an internal region, particularly a hydrophobic interior region, of the protein; and (b) substituting one or more of the amino acid residues within the internal region of the protein with one or more ionizable amino acid residues, wherein the one or more ionizable amino acid residues titrate with a $pK_a$ value shifted relative to the normal $pK_a$ value in water for the one or more ionizable amino acid residues; thereby engineering the non-naturally occurring protein comprising an artificial pH-sensitive conformational switch that responds to a change in pH by causing a global unfolding of the protein. An ionizable amino acid residue that titrates with a $pK_a$ value shifted relative to the normal $pK_a$ value in water for the ionizable amino acid residue may be said to have an "anomalous $pK_a$ value." An "anomalous $pK_a$ value" for an ionizable amino acid residue as used herein refers to a $pK_a$ value that differs from the $pK_a$ value of the ionizable amino acid residue in water by at least about ±0.1, ±0.2, ±0.3, ±0.4, ±0.5, ±0.6, ±0.7, ±0.8, ±0.9, ±1.0, ±1.1, ±1.2, ±1.3, ±1.4, ±1.5, ±1.6, ±1.7, ±1.8, ±1.9, ±2.0, ±2.1, ±2.2, ±2.3, ±2.4, ±2.5, ±2.6, ±2.7, ±2.8, ±2.9, ±3.0, ±3.1, ±3.2, ±3.3, ±3.4, ±3.5, ±3.6, ±3.7, ±3.8, ±3.9, ±4.0, ±4.1, ±4.2, ±4.3, ±4.4, ±4.5, ±4.6, ±4.7, ±4.8, ±4.9, ±5.0, ±5.1, ±5.2, ±5.3, ±5.4, ±5.5, ±5.6, ±5.7, ±5.8, ±5.9, ±6.0, ±6.1, ±6.2, ±6.3, ±6.4, ±6.5, ±6.6, ±6.7, ±6.8, ±6.9, ±7.0, ±7.1, ±7.2, ±7.3, ±7.4, ±7.5, ±7.6, ±7.7, ±7.8, ±7.9, ±8.0, ±8.1, ±8.2, ±8.3, ±8.4, ±8.5, ±8.6, ±8.7, ±8.8, ±8.9, ±9.0, ±9.1, ±9.2, ±9.3, ±9.4, ±9.5, ±9.6, ±9.7, ±9.8, ±9.9, ±10.0, or more.

In another particular aspect of the presently disclosed subject matter, the one or more ionizable amino acid residues that titrate with a $pK_a$ value shifted relative to the normal $pK_a$ value in water for the one or more ionizable amino acid residues are selected from the group consisting of Lys, Asp, and Glu.

In some embodiments of the presently disclosed subject matter, the protein comprising the artificial pH-sensitive conformational switch unfolds within a range of pH from about 5.0 pH to about 9.0 pH, particularly from at least about 5.1 pH, 5.2 pH, 5.3 pH, 5.4 pH, 5.5 pH, 5.6 pH, 5.7 pH, 5.8, pH, 5.9 pH, 6.0 pH, 6.1 pH, 6.2 pH, 6.3 pH, 6.4, pH, 6.5 pH, 6.6 pH, 6.7 pH, 6.8, pH, 6.9 pH, 7.0 pH, 7.1 pH, 7.2 pH, 7.3 pH, 7.4, pH, 7.5 pH, 7.6 pH, 7.7 pH, 7.8 pH, 7.9 pH, 8.0 pH, 8.1 pH, 8.2 pH, 8.3 pH, 8.4 pH, 8.5 pH, 8.6 pH, 8.7 pH, 8.8 pH, or 8.9 pH, up to about 9.0 pH. In some embodiments of the presently disclosed subject matter, the protein comprising the artificial pH-sensitive conformational switch unfolds within a range of pH from about 6.5 pH to about 7.5 pH. In some embodiments of the presently disclosed subject matter, the protein comprising the artificial pH-sensitive conformational switch unfolds at a pH of about 7.0 pH. In some embodiments of the presently disclosed subject matter, the protein comprising the artificial pH-sensitive conformational switch unfolds within a physiological pH range. "Physiological pH range" as used herein refers to the range of pH encompassing the pH of cellular and bodily fluids such as cytosol, blood, and cerebrospinal fluid, comprising a range from about 7.2 pH to about 7.5 pH, more particularly from about 7.3 pH to about 7.5 pH, and even more particularly from about 7.34 pH to about 7.45 pH.

B. Model Staphylococcal Nuclease and Variants

In another embodiment, the methods of the presently disclosed subject matter for producing a protein comprise producing a model staphylococcal nuclease (SNase) protein comprising an artificial pH-sensitive conformational switch that responds to a change in pH by causing a global unfolding of the protein.

SNase (also known as Micrococcal nuclease) is a monomeric $Ca^{++}$ dependent enzyme of 149 amino acids (SEQ ID NO:1) that is an endo-exonuclease that catalyzes hydrolysis of double- or single-stranded DNA and RNA via endonucleolytic cleavage to 3'-phosphomononucleotide and 3'-phospholigonucleotide end-products.

SNase is a rich model system for detailed examination of structural plasticity and structure-energy correlations. The thermodynamic stability of SNase can be modulated with mutagenesis and increased from 5.4 kcal/mol for the wild type protein (Stites et al., J. Mol. Biol. 221: 7-14 (1991)) to nearly 12 kcal/mol for two highly stable variants known as NVIAGA (SEQ ID NO:2; Baran et al., J. Mol. Biol. 379: 1045-1062 (2008)), and Δ+PHS (SEQ ID NO:3; García-Moreno et al., Biophys. Chem. 64: 211-224 (1997)). The Δ+PHS protein, engineered by a deletion (44 to 49) and five substitutions (P117G, H124L and S128A, G05F and V15N), is of special interest because it has been shown to tolerate the presence and ionization of groups buried in its hydrophobic core (García-Moreno et al., Biophys. Chem. 64: 211-224 (1997); Castañeda et al., Proteins 77:570-588 (2009); Chimenti et al., J. Mol. Biol. 405:361-377 (2011); Fitch et al., Biophys. J. 82:3289-3304 (2002); Isom et al., Proc. Natl. Acad. Sci. U.S.A. 105:17784-17788 (2008); Karp et al., Biophys. J. 92:2041-2053 (2007); Karp et al., Biochemistry. 49:4138-4146 (2010); Takayama et al., J. Am. Chem. Soc. 130:6714-6715 (2008)). The majority of variants of Δ+PHS with internal ionizable groups retain a folded structure and cooperative unfolding profiles (Castañeda et al., Proteins 77: 570-588 (2009); Karp et al., Biophys. J. 92:2041-2053 (2007)), even when the internal groups are charged.

Accordingly, in some embodiments of the presently disclosed subject matter, the SNase is selected from the group consisting of: (a) wild-type SNase comprising the amino acid sequence of SEQ ID NO:1 or a functional variant thereof; (b) Δ+NVIAGLA comprising the amino acid sequence of SEQ ID NO:2 or a functional variant thereof; (c) Δ+PHS comprising the amino acid sequence of SEQ ID NO:3 or a functional variant thereof; and (d) a functional variant of wild-type SNase having a thermodynamic stability that is at least 3 kcal/mol greater than wild-type SNase.

"Functional variants" of SNase include functional fragments, functional mutant proteins, and/or functional fusion proteins. A functional variant of SNase refers to an isolated and/or recombinant protein or polypeptide which has at least one property, activity and/or function characteristic of SNase, such as catalyzing hydrolysis of double- or single-stranded DNA and RNA via endonucleolytic cleavage to 3'-phosphomononucleotide and 3'-phospholigonucleotide end-products. Generally, fragments or portions of SNase encompassed by the presently disclosed subject matter include those having a deletion (i.e. one or more deletions) of an amino acid (i.e., one or more amino acids) relative to the wild-type SNase (such as N-terminal, C-terminal or internal deletions). Fragments or portions in which only contiguous amino acids have been deleted or in which non-contiguous amino acids have been deleted relative to wild-type SNase are also envisioned. Generally, mutants or derivatives of SNase encompassed by the present invention include natural or artificial variants differing by the addition, deletion and/or substitution of one or more contiguous or non-contiguous amino acid residues, or modified polypeptides in which one or more residues is modified, and mutants comprising one or more modified residues. Preferred mutants are natural or artificial variants of SNase differing by the addition, deletion and/or substitution of one or more contiguous or non-contiguous amino acid residues.

Generally, the SNase or functional variant thereof has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:1, SEQ ID NO:2, or SEQ ID NO:3 over the length of the variant.

In some embodiments, the amino acid sequences of SEQ ID NO:1, SEQ ID NO:2, or SEQ ID NO:3 are used to make purified protein of SNase, for example, using currently available recombinant protein production Amino acid sequence identity can be determined using a suitable amino acid sequence alignment algorithm. SNase proteins and functional variants thereof can be produced using well-known methods, such as recombinant expression and purification, chemical synthesis (e.g., synthetic peptides), or by combinations of biological and chemical methods, and recombinant proteins or polypeptides which are isolated. The proteins can be obtained in an isolated state of at least about 50% by weight, preferably at least about 75% by weight, and more preferably, in essentially pure form. Proteins or polypeptides referred to herein as "recombinant" are proteins or polypeptides produced by the expression of recombinant nucleic acids.

"Sequence identity" or "identity" in the context of proteins or polypeptides refers to the amino acid residues in two amino acid sequences that are the same when aligned for maximum correspondence over a specified comparison window.

Thus, "percentage of sequence identity" refers to the value determined by comparing two optimally aligned sequences over a comparison window, wherein the portion of the amino acid sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized. The "Clustal V method of alignment" corresponds to the alignment method labeled Clustal V (described by Higgins and Sharp, CABIOS. 5:151-153 (1989); Higgins, D. G. et al. (1992) Comput. Appl. Biosci. 8:189-191) and found in the MegAlign™ program of the LASERGENE bioinformatics computing suite (DNASTAR Inc., Madison, Wis.).

It is well understood by one skilled in the art that many levels of sequence identity are useful in identifying proteins or polypeptides (e.g., from other species) wherein the proteins or polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

In particular embodiments of the presently disclosed subject matter, substituting each of the one or more amino acid residues with one or more alternative amino acid residues comprises substituting amino acid residues in wild-type SNase comprising the amino acid sequence of SEQ ID NO:1 or a functional variant thereof, wherein the amino acid substitutions in SEQ ID NO:1 are selected from the group consisting of: (a) V74E and N100E; (b) T62E and L125E; (c) V66E and L125E; (d) L36E and A58E; (e) V66E and A109E; (f) T62E and V104E; (g) I72D and N100E; (h) L36K and L103K; (i) L36K and A109K; (j) T41K and I92K; (k) T41K and V99K; (l) T62K and L125K; and (m) V66K and A109K.

In other particular embodiments of the presently disclosed subject matter, substituting each of the one or more amino acid residues with one or more alternative amino acid residues comprises substituting amino acid residues in Δ+NVIAGLA comprising the amino acid sequence of SEQ ID NO:2 or a functional variant thereof, wherein the amino acid substitution is V23E.

In other particular embodiments of the presently disclosed subject matter, substituting each of the one or more amino acid residues with one or more alternative amino acid residues comprises substituting amino acid residues in Δ+PHS comprising the amino acid sequence of SEQ ID NO:3 or a functional variant thereof, wherein the amino acid substitutions in SEQ ID NO:3 are selected from the group consisting of: (a) L36K and A109K; (b) L36K and L103K; (c) T41K and A192K; (d) T62K and L125K; (e) L36K and A109K; (f) T41K and V99K; (g) V66K and A109K; and (h) V23E.

II. Proteins Comprising An Artificial Ph-Sensitive Conformational Switch Within An Internal Region In another embodiment, the presently disclosed subject matter provides a protein produced by any of the methods described herein. In particular, the presently disclosed subject matter provides a protein comprising a non-naturally occurring protein comprising an artificial pH-sensitive conformational switch that responds to a change in pH by causing a global unfolding of the protein, wherein the one or more ionizable amino acid residues titrate with a pKa value shifted relative to the normal pKa value in water for the one or more ionizable amino acid residues. In a particular aspect, the one or more ionizable amino acid residues have been substituted for one or more amino acid residues in an internal region of the protein, particularly a hydrophobic interior region of the protein.

Accordingly, in some embodiments of the presently disclosed subject matter, the protein comprising the artificial pH-sensitive conformational switch that responds to a change in pH by causing a global unfolding of the protein unfolds within a range of pH from about 5.0 pH to about 9.0 pH, particularly from at least about 5.1 pH, 5.2 pH, 5.3 pH, 5.4 pH, 5.5 pH, 5.6 pH, 5.7 pH, 5.8, pH, 5.9 pH, 6.0 pH, 6.1 pH, 6.2 pH, 6.3 pH, 6.4, pH, 6.5 pH, 6.6 pH, 6.7 pH, 6.8, pH, 6.9 pH, 7.0 pH, 7.1 pH, 7.2 pH, 7.3 pH, 7.4, pH, 7.5 pH, 7.6 pH, 7.7 pH, 7.8 pH, 7.9 pH, 8.0 pH, 8.1 pH, 8.2 pH, 8.3 pH, 8.4 pH, 8.5 pH, 8.6 pH, 8.7 pH, 8.8 pH, or 8.9 pH, up to about 9.0 pH. In some embodiments of the presently disclosed subject matter, the protein comprising the artificial pH-sensitive conformational switch that responds to a change in pH by causing a global unfolding of the protein unfolds within a range of pH from about 6.5 pH to about 7.5 pH. In some embodiments of the presently disclosed subject matter, the protein comprising the artificial pH-sensitive conformational switch that responds to a change in pH by causing a global unfolding of the protein unfolds at a pH of about 7.0 pH. In some embodiments of the presently disclosed subject matter, the protein comprising the artificial pH-sensitive conformational switch that responds to a change in pH by causing a global unfolding of the protein unfolds within a physiological pH range as described elsewhere herein.

In a particular embodiment, the one or more ionizable amino acid residues that titrate with a $pK_a$ value shifted relative to the normal $pK_a$ value in water for the one or more ionizable amino acid residues have been substituted for one or more amino acid residues in an internal region of the protein, particularly a hydrophobic interior region of the protein.

In some embodiments of the presently disclosed subject matter, the protein comprising the artificial pH-sensitive conformational switch that responds to a change in pH by causing a global unfolding of the protein comprises one or more ionizable amino acid residues that titrate with a $pK_a$ value shifted relative to the normal $pK_a$ value in water for the one or more ionizable amino acid residues. In a particular embodiment, the one or more ionizable amino acid residues that titrate with a $pK_a$ value shifted relative to the normal $pK_a$ value in water for the one or more ionizable amino acid residues are selected from the group consisting of Lys, Asp, and Glu.

In another embodiment, the proteins of the presently disclosed subject matter comprising an artificial pH-sensitive conformational switch that responds to a change in pH by causing a global unfolding of the protein comprise a model SNase, wherein the SNase is selected from the group consisting of: (a) wild-type SNase comprising the amino acid sequence of SEQ ID NO:1 or a functional variant thereof; (b) Δ+NVIAGLA comprising the amino acid sequence of SEQ ID NO:2 or a functional variant thereof; (c) Δ+PHS comprising the amino acid sequence of SEQ ID NO:3 or a functional variant thereof; and (d) a functional variant of wild-type SNase having a thermodynamic stability that is at least 3 kcal/mol greater than wild-type SNase.

Accordingly, in some embodiments of the presently disclosed subject matter, the one or more ionizable amino acid residues that titrate with a pKa value shifted relative to the normal pKa value in water for the one or more ionizable amino acid residues in the hydrophobic interior region of wild-type SNase comprise amino acid substitutions in SEQ ID NO:1 selected from the group consisting of: (a) V74E and N100E; (b) T62E and L125E; (c) V66E and L125E; (d) L36E and A58E; (e) V66E and A109E; (f) T62E and V104E; (g) I72D and N100E; (h) L36K and L103K; (i) L36K and A109K; (j) T41K and I92K; (k) T41K and V99K; (l) T62K and L125K; and (m) V66K and A109K.

In other embodiments of the presently disclosed subject matter, the one or more ionizable amino acid residues that titrate with a pKa value shifted relative to the normal pKa value in water for the one or more ionizable amino acid residues in the hydrophobic interior region of Δ+NVIAGLA comprise an amino acid substitution in SEQ ID NO:2, wherein the amino acid substitution is V23E.

In other embodiments of the presently disclosed subject matter, the one or more ionizable amino acid residues that titrate with a pKa value shifted relative to the normal pKa value in water for the one or more ionizable amino acid residues in the hydrophobic interior region of Δ+PHS comprise amino acid substitutions in SEQ ID NO:3 selected from the group consisting of: (a) L36K and A109K; (b) L36K and L103K; (c) T41K and A192K; (d) T62K and L125K; (e) L36K and A109K; (f) T41K and V99K; (g) V66K and A109K; and (h) V23E.

III. General Definitions

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Engineering of Artificial pH-Sensing Staphylococcal Nuclease Based on Internal Ionizable Groups with Anomalous $pK_a$ Values By engineering 100 variants of staphylococcal nuclease (SNase) with Lys, Arg, Asp, and Glu at internal positions, the presently disclosed subject matter shows that specialized structural adaptations are not required for highly stable proteins to tolerate buried ionizable groups (Isom et al., Proc. Natl. Acad. Sci. USA 107, 16096-16100 (2010); Isom et al., Proc. Natl. Acad. Sci. USA 108: 5260-5265 (2011); Harms et al., Proc. Natl. Acad. Sci. USA 108: 18954-18959 (2011); Cannon, Johns Hopkins University, PhD thesis (2008)). The majority of SNase variants with internal ionizable groups are stable and their structures are almost indistinguishable from those of the parent protein (Dwyer et al., Biophys. J. 79: 1610-1620 (2000)). However, recent systematic NMR spectroscopy experiments have shown that the ionization of the internal groups can promote structural reorganization of varying amplitude (Chimenti et al., Structure 20: 1071-1085 (2012)). This reorganization is of interest as it explains the structural origins of the relatively high apparent polarizability frequently reported by internal ionizable groups, and because it suggests mechanisms for energy transduction driven by conformational rearrangement in response to the creation of charge in hydrophobic environments (Dwyer et al., Biophys. J. 79: 1610-1620 (2000); García-Moreno et al., Biophys. Chem. 64: 211-224 (1997)).

Materials and Methods

Protein engineering: The Val-to-Glu substitution was introduced into a highly stable variant of SNase known as Δ+NVIAGLA, which has four substitutions (D21N, T33V, T41I and S59A) in addition to those which define the stabilized variant of SNase, Δ+PHS. Protein purification and manipulations were performed as described previously (García-Moreno et al., Biophys. Chem. 64: 211-224 (1997); Shortle et al., Biochemistry 27: 4761-4768 (1988)).

Crystallography: Crystals of ΔΔ+NVIAGLA/V23E were grown at 4° C. using hanging drop vapor-diffusion method by mixing 4.0 μL protein solution (9.6 mg/mL) with 4.0 μL reservoir solution containing 25 mM potassium phosphate (pH 8), 38% 2-methyl-2,4-pnetadiol (MPD) (v/v), 3 molar equivalents of calcium chloride, and 2 molar equivalents of thymidine-3',5'-diphosphate (pdTp). Crystals appeared within 2-3 weeks and were suspended in mother liquor in a Cryoloop™ before being flash-cooled in liquid nitrogen for storage. Data were collected at 100 K on the X25 beamline at Brookhaven National Laboratory using a wavelength of 0.98 Å. Reflections were indexed, integrated, scaled and merged using HKL2000. Initial phasing by molecular replacement was performed with PHASER (McCoy et al., Acta Crystallogr. D 61: 458-464 (2005)) using coordinates of the Δ+PHS protein (PDB ID 3BDC; Castañeda et al., Proteins 77: 570-588 (2009)) as a search model without heteroatoms. Residues 15-24 were omitted and residues 33, 41, 59 and 113 to 116 were truncated to Ala and all β-factors were set to 20 Å (Rose et al., Proc. Natl. Acad. Sci. USA 103: 16623-16633 (2006)) prior to molecular replacement. Iterative model building and refinement were performed using Refmac5 as part of the CCP4 program suite (Bailey, Acta Crystallogr. D 50: 760-763 (1994)) and Coot (Emsley et al., Acta Crystallogr. D 60: 2126-2132 (2004)). The TLSMD server (Painter and Merritt, J. Appl. Crystallogr. 39: 109-111 (2006)) was used to generate TLS motional models used in later refinement iterations. Final checks of structure were done using the SFCHECK (Vaguine et al., Acta Crystallogr. D 55: 191-205 (1999)), PROCHECK (Laskowski et al., J. Appl. Crystallogr. 26: 283-291 (1993)) and MOLPROBITY (Chen et al., Acta Crystallogr. D 66: 12-21 (2010)) servers. The refined satisfactory R values ($R_{work}/R_{free}$=19.0/20.8%) and good Ramachandran statistics (99.2% favored).

NMR spectroscopy: Standard 3D NMR experiments were used to assign $H^N$, Hα, N, Cα, Cβ, and C' a for non-proline residues for Δ+NVIAGLA/V23E variant at pH 4.9 (Yamazaki et al., Biochemistry 32, 5656-5669 (1993), Grzesiek and Bax, J. Am. Chem. Soc. 114: 6291-6293 (1992); Wittekind and Mueller, J. Magn. Reson. B 101: 201-205 (1993)). Data were collected at 298 K on a Bruker Avance 11-600 equipped with a cryoprobe. All spectra were processed with NMRPipe (Delaglio et al., J. Biomol. NMR 6: 277-293 (1995)) and analyzed with Sparky (Goddard and Kneller, SPARKY 3. University of California, San Francisco). Assignments of the Asp and Glu side chain $^{13}C$ resonances, pH titrations and their analysis with the modified Hill equation were performed as described elsewhere (Castañeda et al., Proteins 77: 570-588 (2009)).

Thermodynamic stability: Stability measurements were made using GdnHCl denaturation experiments monitored by intrinsic Trp fluorescence at 296 nm measured with an Aviv Automatic Titrating Fluorometer 105 (Lakewood, N.J.) as described previously (Dwyer et al., Biophys. J. 79: 1610-1620 (2000); García-Moreno et al., Biophys. Chem. 64: 211-224 (1997)). Data at all pH values were analyzed using a two-state model.

Results

FIGS. 1A (Glu) and 1B (Lys) show that ionizable groups with anomalous $pK_a$ values affect the pH dependence of global stability (ΔG°). Internal amino acid positions in staphylococcal nuclease (SNase) were substituted with ionizable groups. The internal positions were selected based on their $pK_a$ values and the global thermodynamic stability, measured previously. The selection of internal positions for substitution with ionizable groups was also based on simulations that assumed perfect additivity (FIG. 2).

In these results, no single Lys or Asp/Glu residues were shown to acid unfold SNase near physiological pH, but many combinations with two internal Lys or Glu achieved the desired result (FIGS. 3 and 4).

FIG. 5 shows $^1H$-$^{15}N$ HSQC spectra monitored as a function of pH for the the Δ+PHS L36K A109K variant, while FIG. 6 shows Far-UV CD measurements for Δ+PHS L36K L103K, Δ+PHS T41K A192K, Δ+PHS T62K L125K, Δ+PHS L36K A109K, Δ+PHS T41K V99K, and Δ+PHS V66K A109K. These results demonstrate conclusively that internal ionizable groups can be used to modify proteins so they undergo cooperative transitions between folded and unfolded states near physiological pH. In general, additivity of the effects of multiple ionizable groups does not hold. These results demonstrate a general strategy for the engineering of switches that can make proteins respond with dramatic conformational changes in response to relatively small changes in pH. Without being bound by theory, it is thought that nature never depends on single ionizable residues with anomalous $pK_a$ values to drive pH sensitive conformational switches because such a switch would not be robust. These results show that this approach can used for the engineering of pH sensitive switches.

Crystal Structures: The V23E substitution has been studied in two highly stable forms of SNase known as Δ+PHS and Δ+NVIAGLA. In Δ+PHS SNase, the $pK_a$ of Glu-23 is 7.1±0.2 (Isom et al., Proc. Natl. Acad. Sci. USA 107, 16096-16100 (2010)) and in the Δ+NVIAGLA variant, the $pK_a$ was 7.5±0.2. The crystal structure of the Δ+PHS/V23E protein at pH 6, where Glu-23 is neutral, is fully folded and almost indistinguishable from that of the reference Δ+PHS protein (FIG. 7). The presently disclosed subject matter shows that in contrast, the high-resolution structure (1.4 Å) of the Δ+NVIAGLA/V23E variant at pH 8, where Glu-23 is charged, is partially folded (FIG. 7). In the partially unfolded state, the β-barrel that forms the OB domain of SNase opens through a movement of β-strands 1 (β-1) and 2 (β-2) (comprising residues 15-24) by as many 18 Å away from the rest of β-barrel. In the partially unfolded, open state, Glu-23, which when neutral is buried fully in the hydrophobic core in the closed structure, is completely exposed to bulk water. The conformational change also exposes the hydrophobic core of the protein to bulk water. Surprisingly, the rest of the protein remains largely unperturbed, even the region with the residues lining the exposed hydrophobic core. The CαRMSD between the closed structures with Glu-23 buried and the open one where it is exposed decreases from 2.6 Å to 0.3 Å when residues 15-24 are omitted. This is comparable to the CαRMSD between Δ+PHS/V23E and the Δ+PHS variant used to engineer it.

Structural Reorganization Monitored by NMR Spectroscopy: The open state observed in the crystal structure of the Δ+NVIAGLA/V23E variant at pH 8 was confirmed in solution with NMR spectroscopy. The $^1H$-$^{15}N$ HSQC spectrum of the Δ+NVIAGLA/V23E variant at pH 4.9 and that of the reference Δ+NVIAGLA protein under acidic conditions showed that the V23E variant was fully folded at low pH values. All resonances in the spectrum of the reference protein were present in the spectrum of the variant. Titration in increments of 0.3 to 0.4 pH units yielded virtually identical behavior for all resonances in the two proteins, except for the residues that comprise β-1 and β-2, part of β-3 and the hydrophobic face of β-1 in V23E variant (FIG. 7). The residues displayed significant line broadening with increasing pH and became undetectable at pH values between pH 6.6 and 7.0 owing to intermediate exchanges (FIG. 8A). The concerted nature of the broadening event and the spatial proximity of the residues involved suggest a conformation change driven by the ionization of Glu-23, which is the only ionizable group in this region of the protein that titrates in this pH range. At pH values between 7.0 and 8.9, the effects of pH on the remaining crosspeaks were comparable for the two proteins and showed no evidence of any further conformational change. Similar behavior was observed in the HSQC spectra of Δ+PHS/V23E variant (FIG. 8B). The carboxyl group of Glu-23 was observed directly using the $^{13}C$-detected CBCGCO experiments that correlates the $C^{β/γ}$-$C^{γ/δ}$ of Asp/Glu with the side chain carboxyl ($C^{\beta/\gamma}$-$C^{\gamma/\delta}$) carbon (Castañeda et al., Proteins 77: 570-588 (2009); FIG. 9). An additional upheld-shifted $pK_a$ ($C^{\beta/\gamma}$=31.4 ppm, $C^{\gamma/\delta}$=174.2 ppm) absent in the reference proteins was observed in the Δ+NVIAGLA/V23E variant from pH 5.7 to pH 4.0, the lowest pH value measured. Standard (H)CC(CO)NH-TOCSY and 2D CBCGCO-TOCSY experiments unambiguously assigned this new peak to Glu-23 in the protonated state (Castañeda et al., Proteins 77: 570-588 (2009); Grzesiek et al., J. Magn. Reson. B 101: 114-119 (1993)). The exact chemical origins of this large upheld shift are not known, but they appear to be characteristic of the $^{13}$C nucleus of the protonated carboxylic groups embedded in a hydrophobic environment (similar chemical shifts were observed for Glu-23 and Asp-66 residues in the Δ+PHS/V23E and Δ+PHS/V66D variants of SNase at pH values below the $pK_a$ of Glu-23 and Asp-66, respectively; Chimenti et al., J. Mol. Biol. 405: 361-377 (2011)). Between pH 5.7 and 7.6, the Glu-23 crosspeak was not visible in any of the CBCGCO spectra, presumably because of exchange broadening as a result of both titration of the carboxyl side chain itself and the concomitant conformational change in the β-1/β-2 region of the protein. Above pH 7.6, the crosspeak was again observable, albeit it appeared to have shifted significantly in both the $C^{\beta/\gamma}$ and $C^{\gamma/\delta}$ dimensions ($C^{\beta/\gamma}$=36.05 ppm, $C^{\gamma/\delta}$=183.9 ppm at pH 8.5), and entered the region of spectrum characteristics of where crosspeaks of charged, surface Glu side chains exposed to water are normally found (FIG. 9). This provides further and clear evidence that in solution at pH values above the $pK_a$ of Glu-23, the opening of the β-barrel has allowed the charged Glu-23 to contact water.

Thermodynamic Stability: The $pK_a$ values of Glu residues sequestered in the hydrophobic interior of proteins are usually higher than the normal $pK_a$ of 4.5 of Glu in water. In the hydrophobic interior, the equilibrium between the charged and the neutral form of Glu is shifted in favor of the neutral form, resulting in anomalous, elevated $pK_a$ values.

$$\Delta\Delta G^{\circ}_{H2O}(pH) = \Delta\Delta G^{\circ}_{mut} - RTln\left(\frac{1+e^{z2.303(pK_a^D-pH)}}{1+e^{z2.303(pK_a^N-pH)}}\right) \quad (1)$$

The apparent $pK_a$ value of the internal Glu-23 was determined by fitting equation (1) to the pH-dependence of the difference in thermodynamic stability between the Δ+NVIAGLA/V23E variant and the Δ+NVIAGLA protein used as reference. The rightmost term in this expression describes the pH-dependent free energy associated with differences in the $pK_a$ of Glu-23 in the denatured state ($pK_a^D$) where Glu-23 is in water, and in the native state ($pK_a^N$), where it is buried in the hydrophobic interior, at least while it is in the neutral state. $\Delta\Delta G^{\circ}_{mut}$ is the pH-independent free energy difference between the variant and reference protein under conditions where the internal Glu is neutral (i.e. below pH 4.5).

It is not obvious why the ionization of Glu-23 in the Δ+NVIAGLA/V23E variant led to a conformational change in the crystal structure. The probability that a protein will populate an alternate conformational state is governed by the difference in free energy between the native and alternative states. The free energy difference between the Δ+NVIAGLA protein and its V23E variant in solution is approximately 4 kcal/mol below pH 5, where Glu is normally almost fully protonated and neutral (FIG. 10). Under these conditions, the β-barrel constituting the OB domain is native-like. At higher pH values, the stability difference is almost 7 kcal/mol owing to the anomalous $pK_a$ of 7.5 of Glu-23 (FIG. 4). Under these conditions the OB domain is open, probably as a result of the smaller energy gap between the fully folded protein and the alternate, partially unfolded conformation. Crystallization of the open conformation may be influenced by the specific mutation used to engineer the Δ+NVIAGLA protein, specifically the T41I and S59A substitutions near the β-1/β-2 region, despite this response being a general feature of ionizing Glu-23 in SNase.

Discussion

The $pK_a$ of Glu-23 in SNase is anomalous because it is buried in a highly hydrophobic environment without sufficiently high polarity or polarizability to compensate for the loss of interactions with water. For this reason the equilibrium between the neutral and charged forms of the carboxylic group is shifted in favor of the neutral state. In the case of Glu-23, its specific $pK_a$ value is determined by the energetics of the shifts from a closed state to a partially unfolded state in which the previously internal, neutral Glu side chain becomes charged and stabilized by interactions with bulk water. In fact, the apparent $pK_a$ of Glu-23 measured experimentally must reflect an energy weighted average of the $pK_a$ values of Glu-23 in two different conformational states of the protein, and it must include a contribution from more normal $pK_a$ and contributions from one much more elevated than the apparent $pK_a$ of 7.5 that was measured.

As a result of this coupling between global stability, conformational state, and the $pK_a$ of the internal Glu-23, the V23E protein effectively acts as a pH-sensing switch that can switch between open and closed conformations in response to a change in pH in the physiological pH range. Naturally occurring pH-sensing switches, such as the hemoglobin tetramer (Perutz, Nature 228: 726-734 (1970)) and the hemagglutinin protein of the influenza virus (Wiley and Skehel, Annu. Rev. Biochem. 56: 365-394 (1987)), tend to encode the switching potential across many residues, each exhibiting a slightly perturbed $pK_a$ value. This ensures that a single mutation that eliminates the residue that acts as the pH sensor does not eliminate the potential to switch. The case of V23E illustrates how the anomalous $pK_a$ values of the internal ionizable groups can be used to engineer artificial, pH-sensing domains where a single residue introduced by mutagenesis in an environment that leads to a highly anomalous $pK_a$ can drive substantial conformational rearrangements of proteins. The case of Glu-23 also offers an exquisite opportunity for testing the ability of structure-based electrostatics calculations to reproduce a relatively modest conformational transition that happens in response to the ionization of a single, internal group.

Internal polar groups are known to promote high energy states and are thought to affect the folding reaction adversely through the preferential stabilization of intermediates (Zheng and Sosnick, J. Mol. Biol. 397,777-788 (2010)). One unique aspect of the presently disclosed subject matter is that the alternative conformation of SNase does not exist simply as a transient, elusive, low population excited state observable only as a ghost in NMR spectra (Bouvignies et al., Nature 477: 111-114 (2011); Hansen et al. J. Biomol. NMR 41: 113-120 (2008)). The partially unfolded states triggered by the V23E substitution, when Glu-23 is charged, exists as the dominant equilibrium species in solution, which is presumably why it could be crystallized. This particular alternative state of SNase has not been observed previously. It is not obvious if this state plays a role as an intermediate populated during the folding reaction of SNase. What is clear is that a systematic study using ionizable groups at other sites could lead to an unprecedented mapping of the conformations of states populated in the energy landscape of SNase, with exact descriptions of the energetics and the corresponding structures (Zheng and Sosnick, J. Mol. Biol. 397,777-788 (2010)).

Internal ionizable groups buried deeply in the hydrophobic interior of proteins usually play essential functional roles. The relatively low abundance of internal ionizable groups suggests that when these types of groups are not needed for function, they are eliminated through evolution, presumably to enhance the stability of the proteins. However, in the laboratory it has been possible to introduce Lys, Arg, Asp, and Glu at 25 internal positions in SNase, and only two of these 100 variants were judged to be unfolded at pH 7 by CD and Trp fluorescence spectroscopy (Isom et al., Proc. Natl. Acad. Sci. USA 107,16096-16100 (2010); Isom et al., Proc. Natl. Acad. Sci. USA 108: 5260-5265 (2011); Harms et al., Proc. Natl. Acad. Sci. USA 108: 18954-18959 (2011); Cannon, Johns Hopkins University, PhD thesis (2008)). All 100 variants of SNase were less stable than the parent protein. Without being bound by theory, this result is consistent with the idea that internal ionizable groups that are not essential for function are eliminated to minimize their deleterious impact on thermodynamic stability. However, many of the 100 variants of SNase are more stable than what is predicted by simple continuum models because the ionizable side chains can find relatively polar microenvironments within the protein interior. Although there is no evidence that the V23E variant of SNase is aggregation prone, without being bound by theory, the demonstration that the ionization of an internal group can trigger structural reorganization that exposes the hydrophobic interior of a protein suggests that internal ionizable groups that are not essential for function are eliminated not only to enhance their stability, but also to enhance the solubility of the protein. The elimination of internal ionizable groups diminishes the probability of a protein encountering pH regimes in which the ionization of the internal group would lead to the exposure of hydrophobic surfaces that could promote aggregation.

The V23E substitution in staphylococcal nuclease buries Glu-23 deeply in its hydrophobic interior. Crystal structures and NMR spectroscopy experiments show that upon ionization of Glu-23, with a $pK_a$ value of 7.5, a β-turn-β motif that is part of the β-barrel that constitutes the OB domain becomes detached from the rest of the β-barrel. This open state is the preferred one when Glu-23 is charged because although in this state the hydrophobic interior of the protein is exposed to water, the charged moiety of Glu-23 is in contact with bulk water. This is a clear example of how the apparent $pK_a$ of an internal group can reflect the average of two very different $pK_a$ values for an ionizable group in two different conformational states and how the measured $pK_a$ can be governed by a relatively large conformational change. Besides illustrating the large amplitude of conformational reorganization that can be triggered by the presence of a single charge in a hydrophobic environment in a protein, this case suggests a strategy useful for stabilizing partial unfolded states in proteins to map folding landscapes or for the engineering of pH-sensitive protein switches. These data constitute a useful benchmark for critical testing of the ability of a computational algorithm to reproduce the simplest possible ligand-driven conformational transitions in a protein.

Example 2

Use of Buried Ionizable Groups with Anomalous $pK_a$ Values for the Engineering of pH Switch Proteins Introduction Tight regulation of physiological pH is the single most important organizing principle common to all living systems. pH homeostasis is complex and involves the coupled regulation of chemical potentials of all ionic species, water, and osmolytes across bilayers. There are small but meaningful differences in the pH of mitochondria (pH 7.5) extracellular spaces (pH 7.4), cytosol (pH 7.2), and endosomal, lysosomal, ER, and Golgi pH, which are all lower. Nowhere is cellular pH constant; it changes as part of normal physiological processes. This is the case with acidification of exercised muscle when it begins to operate under hypoxic conditions, with cytosolic acidification in apoptotic cells, or acidification as part of the normal maturation of endosomes and lysosomes. Cellular pH can also change as a result of trauma and disease, as is the case of acidification of ischemic tissue after stroke, and most notably the reversal of extracellular and cytosolic pH gradients leading to acidification of cancerous tumors through the Warburg effect (Warburg, Science 123: 309-314 (1956); Vander Heiden et al., Science 324: 1029-1033 (2009)).

Not surprisingly, given how tightly regulated intracellular pH is, many proteins have evolved to interpret small changes in pH as important biochemical signals that modulate biological activity. These proteins act as pH switches, responding to small changes in physiological pH with a conformational change sufficient to affect their activity. Protein pH switches are abundant. For example, human hemoglobin undergoes a conformational transition under the acidic conditions of exercised muscle. This conformational change lowers hemoglobin's affinity for oxygen, thus ensuring delivery of oxygen where it is needed (Riggs, Ann. Rev. Physiol. 50: 181-204 (1988)). The haemagluttinin protein on the lipid bilayer of the influenza virus undergoes a global conformational transition when the virus is exposed to the acidic conditions of the endosome. This conformational change triggers fusion of the viral and endosomal bilayers necessary for the release of the nucleocapsid into the cytoplasm (Bullough et al., Nature 371: 37-43 (1994); Wiley and Skehel, Annu. Rev. Biochem. 56: 365-394 (1987). Similar responses are present in flaviviruses (Fritz et al., J. Cell Biol. 183: 353-361 (2008)) and in HIV, where viral proliferation is triggered by a pH-mediated response (Fledderman et al., Biochemistry 49: 9551-9562 (2010)). pH is known to affect cell proliferation, migration, and tumor development (Martin et al., Am. J. Physiol. Cell. Physiol. 300: 409-495 (2011); Christofk et al., Nature 452: 230-233 (2008); Ihara et al., Proc. Natl. Acad. Sci. U.S.A. 107: 17309-17314 (2010); Frantz et al., J. Cell. Bio. 183: 865-879 (2008); DiGiammarino et al., Nat. Struct. Bio. 9: 12-16 (2002)). Compartmental pH affects trafficking (Hurtado-Lorenzo et al., Nat. Cell. Bio. 8: 124-136 (2006); Hanakam et al., EMBO J. 15: 2935-2943 (1996)), targeting (Lee et al., Proc. Natl. Acad. Sci. U.S.A. 102: 13052-13057 (2005)), and protein degradation (Marshansky, Biochem. Soc. Trans. 35:1092-1099 (2007). pH plays a role in multidrug efflux (Steed et al., Biochemistry 52: 7964-7974 (2013)), ion channel passage (Gonzalez et al., Biochem. J. 422: 57-63 (2012); Raimondo et al., Front. Cell. Neurosci. 7: 202 (2013); Steidl and Yool, Mol. Pharmacol. 55: 812-820 (1999)), pheromone binding (Katre et al., J. Bio. Chem. 284: 32167-32177 (2009)), angiogenesis (Yang et al., Mol. Cell. Bio. 27: 1334-1347 (2007)), and ciliary beat frequency (Sutto et al., J. Physio. 560: 519-532 (2004)). Progression of apoptosis involves cytosolic acidification (Lagadic-Gossmann et al., Cell Death Diff. 11: 953-961(2004)). Many protein aggregation disorders have been observed to be pH-responsive, including Alzheimer's disease (Burdick et al., J. Bio. Chem. 267: 545-554 (1992)), Familial Alzheimer's (Coffey et al., Neuroscience 263: 111-124 (2014)), Parkinson's (Buell et al., Proc. Natl. Acad. Sci. U.S.A. 111: 7671-7676 (2014)), Prion diseases (Swietnicki et al., J. Bio. Chem. 272: 27517-27520 (1997)), and type-2 diabetes (Jha et al., Biochemistry 53: 300-310 (2014)). Although global understanding of the pH-sensing machinery in cells is lacking, the molecular mechanisms whereby proteins drive key biological processes initiated by changes in physiological pH are beginning to be understood.

There is considerable interest in the development of artificial pH sensing proteins for biotechnological applications (Srivastava et al., Physiology. 22: 30-39 (2007)). Small, pH-dependent peptides have been developed for delivery of therapeutic agents into cells (Li et al., Adv. Drug. Deliv. Rev. 56: 967-985 (2003)) or for targeting cancerous tumours for imaging purposes (Reshetnyak et al., Proc. Natl. Acad. Sci. U.S.A. 103: 6460-6465 (2006)). pH dependent fluorescent probes have been developed for quantitative determination of intracellular pH (Wachter et al., Structure 6: 1267-1277 (1998); Bagar et al., Eukary. Cell. 8: 703-712 (2009); Orij et al., Microbiology 155: 268-278 (2008); Shen et al., Mol. Plant. 6: 1419-1437 (2013); Martiniere et al., Plant Cell 25:4028-4043 (2013); Bizzarri et al., Biophys. J. 90: 3300-3314 (2006); Valkonon et al., Appl. Environ. Microbiol. 79: 7129-7187 (2013); Maresova et al., Yeast 27: 317-325 (2010); Poea-Guyon et al., Anal. Bioanal. Chem. 405(12):3983-7 (2013); Hanakam et al., EMBO J. 15: 2935-2943 (1996)). There is potential to modulate responses in cells using engineered alternate-frame folding (Stratton and Loh, Proteins 78:3260-3269 (2010); Stratton and Loh, Prot. Sci. 20: 19-29 (2011)) or allosteric coupling (Wright et al., Proc. Natl. Acad. Sci. U.S.A. 108: 16206-16211 (2011); Sagermann et al. Prot. Sci. 18: 217-228 (2008)). A pH switch can be used to purify specific proteins of therapeutic interest (Strauch et al., Proc. Natl. Acad. Sci. U.S.A. 111: 675-680 (2014)), or modify them to improve efficacy (Igawa et al., Nat. Biotech. 28: 1203-1207 (2010); Chaparro-Riggers et al., J. Bio. Chem. 287:11090-11097 (2012); Berbasova et al., JACS. 135: 1611-16119 (2013)). There is interest in the development of pH-sensitive antibodies for immunotherapeutic purposes (Murtaugh et al., Prot. Sci. 20: 1619-1631 (2011)), antibodies that could, for example, distinguish between normal and cancerous teaching solely on the basis of the more acidic pH in the cancerous tumors.

The thermodynamic principles behind pH sensing are well established (Bell-Upp et al., Biophys. Chem., 159:217-226 (2011)). The pH sensing ability of proteins involves pH-driven conformational changes that depend on differential proton binding between two different conformational states. This requires that ionizable groups in the different conformational states titrate with different $pK_a$ values. When the pH sensing capacity of a protein is essential for biological function, the structural motif that acts as the pH sensor must be robust. The pH-sensor must be immune to the vagaries of mutations. This might explain why, in the cases of hemoglobin, haemagluttinin and other natural pH sensing proteins, the pH sensing motifs involve small contributions from many ionizable groups. Most of these motifs involve histidine residues because they are, normally, the ionizable residues with $pK_a$ values near the physiological range.

Engineering novel pH-sensing proteins by emulating the naturally occurring pH sensors based on histidine residues is extremely challenging, if not impossible (Bell-Upp et al., Biophys. Chem., 159:217-226 (2011)). It is not yet possible to engineer surface groups with specific $pK_a$ values, or even to modulate $pK_a$ values at will with mutagenesis; all efforts to do this invariably also modify the global thermodynamic stability of the protein, which is another key variable that governs pH sensing properties of proteins. To engineer a distributed network of ionizable residues that could act as a pH sensing motif, one would need to either introduce new charges or expertly manipulate the $pK_a$ values of existing ones, a challenge that cannot currently be overcome with computational or with rational design methods.

Here a novel approach is introduced for the engineering of pH sensing proteins based on Lys or Glu residues buried in the hydrophobic interior of proteins. This strategy is based on two observations: (1) Lys, Asp and Glu buried in the hydrophobic interior of a protein have anomalous $pK_a$ values shifted by as many as 5 units from the normal $pK_a$ of 10.4, 4.5 and 4.0 of Lys, Glu, and Asp in water, respectively. These anomalous $pK_a$ values fall within the physiological pH range and are thus useful to sense changes in pH in this range. (2) The thermodynamic stability of proteins with ionizable groups with these highly anomalous $pK_a$ is pH sensitive. A single buried Lys with a depressed $pK_a$ changes the stability of the protein by 1.36 kcal/mol per pH unit away from the normal $pK_a$ of 10.4 for Lys in water. The ionization of these buried groups can trigger local or global conformational transitions.

Previous efforts shown hereinabove have resulted in the engineering of a library of variants of staphylococcal nuclease (SNase) with Lys, Asp and Glu buried at 25 internal positions. The majority of these internal residues titrate with anomalous $pK_a$ values, many of them near 7. Lys residues with $pK_a$ values near 5, and carboxylic residues with $pK_a$ values higher than 10 have already been engineered in SNase. Trp fluorescence and circular dichroism and NMR spectroscopy showed that, with two exceptions, the variants tolerated the presence of the buried ionizable group in both the neutral and the charged state, and that they are mostly folded at pH 7.

The library of anomalous $pK_a$ values for buried Lys, Asp and Glu in SNase enable testing of a new design principle for the engineering of pH sensing proteins based on the burial of ionizable groups with anomalous $pK_a$ values. In accordance with what was expected based strictly on the principles of linkage thermodynamic, it has been demonstrated that pairs of internal Lys or Glu are sufficient for the engineering of pH switch proteins that unfold cooperatively in response to a modest change in pH in the physiological range.

Materials and Methods

Proteins: All variants were engineered with the Δ+PHS background of SNase using the QuickChange kits and purified following the protocol previously described (Garcia-Moreno et al., Biophys. Chem. 64: 211-224 (1997); Shortie et al., Biochemistry 27:4761-4768 (1988)).

pH Titration Monitored by Trp Fluorescence and CD Spectroscopy: Acid-base titrations monitored by changes in circular dichroism (CD) were performed with an Aviv CD spectrometer model 215 (Lakewood, N.J.). Titrations that monitored Trp fluorescence were performed with an Aviv Automatic Titrating Fluorometer 105. All data were collected at 25° C. in 100 mM KCl following procedures published previously (Isom et al., Proc. Natl. Acad. Sci. U.S.A. 107: 16096-16100 (2010); Isom et al., Proc. Natl. Acad. Sci. U.S.A. 108: 5260-5265 (2011)). Each sample was prepared with a protein concentration of ~50 ug/mL with a buffer mixture consisting of 6.25 mM each of KAcetate, MES, Tris, and CHES in 100 mM KCl. Titrant was 0.3N KOH or HCl. Midpoints of pH-driven transitions were obtained by non-linear least squares fits with a two state model.

Thermodynamic stability: Guanidine hydrochloride (GdnHCl) titrations were performed with an Aviv Automatic Titrating Fluorometer 105 to measure thermodynamic stability over a wide range of pH values. All data were collected at 25° C. Samples were prepared with a protein concentration of ~50 ug/mL in 100 mM KCl. The buffers varied based on the pH of the measurement: 25 mM CAPS, 25 mM CHES, or 25 mM HEPES were used for pH ranges 9.5-10, 8-9, and 7-7.5, respectively. The titrant was 6M GdnHCl in the appropriate buffer. The titrations were performed as described previously (Dwyer et al., Biophys. J. 79: 1610-1620 (2000); Garcia-Moreno et al., Biophys. Chem. 64: 211-224 (1997)).

NMR spectroscopy: $^1$H-$^{15}$N HSQC experiments were measured for the V66E/A109E and T62K/L125K variants. Following previously established protocols, samples were split in two, one for titrating with acid and one for base. Data were collected at 298K on a Bruker Avance II-600 equipped with a cryoprobe. All spectra were processed with NMRPipe (Delaglio et al., J. Biomol. NMR 6: 277-293 (1995)) and analyzed with Sparky (Goddard and Kneller, SPARKY 3. University of California, San Francisco).

X-ray crystallography: Crystals of the V66E/A109E variant were grown using hanging-drop vapor diffusion. Protein concentration was 8.0 mg/mL. Crystals were grown with a 2/1/1 molar ratio of $CaCl_2$ to 3'-5'-thymidine diphosphate to protein in 25 mM phosphate at 4° C. at pH 6.0 and 30% MPD (Table 1). Crystals were flash cooled in liquid nitrogen. Diffraction data were collected using a Bruker Duo Apex diffractometer. Frames were processed using Bruker's software. Initial phases were obtained by molecular replacement methods in Phaser using the following search model: Δ+PHS (PDB id:3BDC) with solvent and heteroatoms removed, all b-factors set to 20.0 $Å^2$ and side chains truncated to Ala at the mutation site and disordered side chains. Iterative model building and refinement were performed in Coot and the Refmac 5 suite of CCP4. Refinements were performed until convergence of Rfactor and Rfree. TLS refinement was performed.

TABLE 1

| Crystallographic parameters | |
|---|---|
| Variant | V66E A109E |
| PDB Code | 4OL7 |
| Crystallization Condition | |
| MPD (%) | 30 |
| pH | 6.0 |
| Data Collection | |
| Wavelength (Å) | 1.54 |
| Space Group | $P2_12_12_1$ |
| Cell Dimensions | |
| a (Å) | 47.15 |
| b (Å) | 54.16 |
| c (Å) | 108.13 |
| α (°) | 90.00 |
| β (°) | 90.00 |

TABLE 1-continued

| Crystallographic parameters | |
|---|---|
| γ (°) | 90.00 |
| Resolution range[a] (Å) | 50.0-1.67 |
| | (1.69-1.67) |
| No. of unique reflections | 32967 (1147) |
| Completeness (%) | 99.8 (100.0) |
| Redundancy | 13.0 (5.6) |
| Average I/σ (I) | 29.3 (4.4) |
| $R_{sigma}$ | 0.026 (0.228) |
| Wilson B (Å$^2$) | 22.1 |
| Refinement | |
| Resolution range (Å) | 48.47-1.67 |
| | (1.71-1.67) |
| Total no. of unique reflections | 32906 (2242) |
| No of reflections in test set | 1669 (148) |
| $R_{work}$ | 0.158 (0.181) |
| $R_{free}$ | 0.191 (0.249) |
| RMS distance for ideal geometry | |
| Bond (Å) | 0.016 |
| RMS angle (°) | 1.80 |
| Average B-factors (Å$^2$) | |
| Protein (no. of atoms) | 14.0 (2297) |
| Solvent (no. of atoms) | 23.1 (290) |
| Ion/Ligand (no. of atoms) | 10.7 (52) |
| Ramachandran Plot | |
| Most favored (%) | 87.8 |
| Additionally allowed (%) | 11.3 |
| Generously allowed (%) | 0.0 |
| Disallowed (%) | 0.8 |
| No. of non-glycine, non-proline and non-end residues | 238 |
| No. of glycine, proline, and end residues | 30 |
| Total no. of residues[b] | 268 |

[a]Values in parentheses correspond to the highest resolution shell
[b]Residues 1-4 in chain B and residues 143-149 from both chains were excluded from refinement because these residues had no visible electron density Results Design Principles: The goal was to modify a highly stable protein that is normal insensitive to pH over a wide range, to allow it to undergo a cooperative transition between fully folded and fully unfolded states in response to a small change in pH in the physiological pH range. The approach involved use of multiple buried Lys or Glu residues that have anomalous $pK_a$ values when the protein is in the fully folded state and normal $pK_a$ values when the protein is unfolded. The $pK_a$ values are anomalous in the fully folded state because charges are incompatible with the hydrophobic and relatively dry interior of proteins; therefore, in the native state the equilibrium between charged and neutral forms of the ionizable moiety shift in favor of the neutral form.

Thermodynamic Principles: The potential for ionizable groups to trigger a conformational transition in response to a change in pH is governed by two factors: (1) the net magnitude of differences in $pK_a$ values of ionizable groups in the two different conformational states (Bell-Upp et al., Biophys. Chem., 159:217-226 (2011)), and (2) the global thermodynamic stability of the protein. Simulations show how a single Lys with $pK_a$ depressed by x, y, or z $pK_a$ units (FIG. 11A), or one, two or three Lys residues with a $pK_a$ depressed by x units (FIG. 11 B) affect the pH dependence of stability of a protein. The single Lys with a depressed $pK_a$ decreases the stability of the protein by 1.36 kcal/mol per pH unit (at 298 K) in the range bracketed by the normal $pK_a$ in the unfolded state and by the depressed $pK_a$ in the native state (FIG. 11A). In contrast, the presence of two or three Lys residues gives rise to a steeper sensitivity to changes in pH, equivalent to destabilization by 1.36, 2.72, or 4.08 kcal/mol per pH unit (FIG. 11B) over a narrower pH range.

The simulations in FIGS. 11A and 11B describe how one, two or three ionizable groups with shifts in $pK_a$ values of different magnitudes can affect the stability of a protein. Whether these groups poise the protein for structural response depends on the balance between the free energy stored in the form of differences in $pK_a$ values and the component of the net difference in the Gibbs free energy ($\Delta\Delta G°_{H2O}=\Delta G°_{H2O}$ (folded)$-\Delta G°_{H2O}$ (unfolded)) that is insensitive to pH. At the pH where the destabilizing effects related to shifted $pK_a$ values and the pH-independent component of stability are equal, the protein will exist in the two different conformational states in equal amounts.

Selection of pH-sensing Moieties: The internal Lys and Glu residues studied previously in SNase were engineered into a highly stable form of SNase known as Δ+PHS after the truncations and substitutions used to engineer it. With the exception of Lys-92 and Lys-104, no single internal Lys or Glu was sufficient to unfold SNase. Simulations based on the experimentally determined thermodynamic stability of the variants and the measured $pK_a$ values were used to identify pairs of Lys or Glu residues likely to trigger global unfolding in the neighborhood of pH 7.4, equivalent to blood pH. In the face of evidence to the contrary, additivity of thermodynamic effects was assumed.

Based on the simulations, two variants were selected for further study, Δ+PHS/T62K/L125K and Δ+PHS/V66E/A109E. The crystal structure of the V66E/A109E protein was obtained whereas the T62K/L125K protein has resisted crystallization (FIG. 12A and Table 1). The structure of the double Glu variant shows that the two Glu residues are indeed internal. The structure of the double variant is almost identical to that of the background Δ+PHS protein with the exception of the loop region comprising residues X to Y.

pH Dependence of Stability of Switch Proteins: The Δ+PHS/T62K/L125K protein was designed to be stable at high pH, where the Lys residues are neutral, and to unfold near pH 7.4, where normally they would be charged. In contrast, the ΔPHS/V66E/A109E variant was designed to be stable at low pH, where carboxylic groups are usually neutral, and to unfold at higher pH, where carboxylic groups are normally charged. This was demonstrated by measurement of thermodynamic stability ($\Delta G°_{H2O}$) as a function of pH using chemical denaturation monitored by Trp fluorescence (FIG. 13A, Table 2). The background protein, ΔPHS, has little to no pH sensitivity between pH 5 and 9 so any change in protein behavior in this region can be attributed to the newly introduced internal Glu or Lys residues. The consequences of the internal Lys or Glu residues on the pH sensitivity of the protein are fully consistent with what observed previously (Isom et al., Proc. Natl. Acad. Sci. U.S.A. 108: 5260-5265 (2011); Isom et al., Proc. Natl. Acad. Sci. U.S.A. 107: 16096-16100 (2010); Isom et al., Proc. Natl. Acad. Sci. U.S.A. 105:17784-17788 (2008)). The data show that $\Delta G°_{H2O}$ approaches 0 near pH 7, consistent with the idea that the proteins are being unfolded near neutral pH in response to the ionization of the pair of internal Lys or Glu residues.

Close examination of the dependence of $\Delta G°_{H2O}$ on pH ($\Delta\Delta G°_{H2O}/pH$ where $\Delta\Delta G°_{H2O}=\Delta G°_{H2O}$(variant)$-\Delta G°_{H2O}$ (background)) was used to examine if one or both ionizable groups play a role in determining the pH sensitivity of the variants. Based on previous studies, it is reasonable to assume that the pH sensitivity of the variants can be largely attributed to the internal Glu and Lys residues. The rate of change of $\Delta G°_{H2O}$ with pH for every shift in $pK_a$ is 1.36 kcal/mol for a single titrating group, or 2.72 kcal/mol for two independently titrating groups. If both Glu-66 and Glu-109 or Lys-62 and Lys-125 have shifted $pK_a$ values, the data in FIG. 11B would fit well with the plotted ideal slopes of ±2.72 kcal/mol/pH. This is the case for ΔPHS/T62K/L125K. The ΔPHS/V66E/A109E variant fits a 2-group slope at pH >5.5 but is closer to a 1-group slope at pH<5.5 indicating that the interactions between E109 and D21 observed in the crystal structure (FIG. 12B) is likely to be playing a role in determining the $pK_a$ values of these groups.

TABLE 2

Thermodynamic parameters extracted from chemical denaturation experiments

| Protein | pH | $\Delta G°_{H2O}$ (kcal/mol) | Cm | m |
|---|---|---|---|---|
| Δ + PHS/T62K/L125K | 9.8 | 4.1 ± 0.1 | 0.7 | 6.1 ± 0.1 |
|  | 9.4 | 3.6 ± 0.4 | 0.6 | 6.1 ± 0.4 |
|  | 9.0 | 3.0 ± 0.3 | 0.5 | 6.2 ± 0.4 |
|  | 8.5 | 2.2 ± 0.4 | 0.3 | 6.2 ± 0.5 |
|  | 8.0 | 1.1 ± 0.5 | 0.2 | 6.0 ± 0.8 |
| Δ + PHS/V66E/A109E | 3.9 | 2.0 ± 0.1 | 0.4 | 4.4 ± 0.1 |
|  | 4.3 | 3.3 ± 0.2 | 0.6 | 4.9 ± 0.1 |
|  | 4.9 | 3.7 ± 0.3 | 0.7 | 5.6 ± 0.1 |
|  | 5.5 | 3.1 ± 0.2 | 0.5 | 6.0 ± 0.2 |
|  | 6.0 | 1.9 ± 0.5 | 0.4 | 5.7 ± 0.7 |
|  | 6.5 | 0.6 ± 0.6 | 0.2 | 5.9 ± 1.2 | pH Switching Behavior: Trp fluorescence, far-UV circular dichroism (222 nm) and NMR spectroscopy were used to demonstrate that the switch proteins switch cooperatively between folded and unfolded states near pH 7.4 and in response to changes in pH.

The region of interest in the acid base titrations by Trp fluorescence (FIG. 14A) and for UV-CD (FIG. 14B) is the one centered near pH 7. The acid titration observed for the double Glu variant (red) is of no special interest; it is shifted to higher pH relative to the background protein (black) because of differences in thermodynamic stability. The midpoints of the unfolding of the double Lys variants monitored by Trp fluorescence and CD 222 nM were 7.5 and 7.4 respectively (Table 3). For the double Glu variant, they were 6.8 and 6.9, respectively (Table 3). The pH switch encoded by the Glu residues is more sensitive than the one encoded by Lys residues, thus the transition between folded and unfolded states is steeper.

TABLE 3

Acid-base titrations

| Protein | Signal | $pH_{mid}$ (major) | $pH_{mid}$ (minor) |
|---|---|---|---|
| Δ + PHS/T62K/L125K | CD (222 nm) | 7.43 + 0.03 | 3.35 + 0.31[a] |
|  | Fluorescence | 7.54 ± 0.05 | — |
| Δ + PHS/V66E/A109E | CD (222 nm) | 6.75 ± 0.01 | — |
|  | Fluorescence | 6.92 ± 0.02 | — |

[a]This transition represents the acid-unfolding of the protein

The double Lys variant exhibited a secondary transition at pH<6, more clearly apparent in the CD spectroscopy data. The baselines for the double Glu variant at pH >7 suggest that the acid unfolded and base unfolded proteins are structurally different. Full CD scans in the far-UV range support the notion that the base unfolded form of the double Glu variant is more structured than the double Lys variant (FIG. 15). Indeed the CD data is consistent with the loss of secondary structure relative to fully folded and unfolded SNase. The spectrum of ΔPHS/V66E/A109E at pH 5, where it is most stable, has minima near 208 nm and 222 nm like that of the fully folded reference spectrum but the ratio is reversed; the signal at 208 nm is stronger than at 222 nm. As the pH increases, there is a further shift in the minima ratio, which is expected of a protein that has lost secondary structure. The spectra for ΔPHS/T62K/L125K show the same shift in the ratio 208 nm to 222 nm when the pH decreased, as expected. The spectrum at pH 9 closely matches that of the folded state while the spectrum at pH 5 behaves similar to that of the unfolded state.

The agreement between the structural transitions reported by fluorescence and by CD was excellent. $^1H$-$^{15}N$ HSQC spectra collected at pH 5.09 and 7.94 for ΔPHS/V66E/A109E, and at pH 6.49 and 8.53 for ΔPHS/T62K/L125K, were used to obtained a more atomistic level of the structural changes involved in the pH switch (FIG. 16). At the high pH, the spectrum for the ΔPHS/T62K/L125K variant is well dispersed and matches closely the spectrum of the background protein (data not shown). At low pH, where the protein was expected to be unfolded, all resonances collapse into the characteristic pattern without dispersion of an unfolded protein. The case of ΔPHS/V66E/A109E is more complex. At pH 5.09, where the protein is expected to be fully folded, the spectrum shows peaks consistent with a fully folded population alongside peaks characteristic of unfolded protein. On the other hand, at pH 7.94, where the protein is expected to be fully unfolded, the spectrum was fully consistent with that of a fully unfolded protein. As shown hereinabove, in water, Lys and Glu titrate with $pK_a$ values of 10.4 and 4.4, respectively, far from the physiological pH range. However, when buried in the hydrophobic interior, the $pK_a$ values of Lys and Glu residues can become highly depressed or elevated, respectively, and achieve values close to physiological. The ionization of these buried groups can drive local or global unfolding of proteins. Two variants of staphylococcal nuclease (SNase) with V66E/A109E or T62K/L125K substitutions were used to demonstrate the utility of buried ionizable groups for design of artificial pH switches. Trp fluorescence and CD and NMR spectroscopy were used to demonstrate that these two variants unfolded globally and cooperatively in response to small changes in pH near pH 7. The variant with internal Lys residues unfolds in response to increases in pH whereas the variant with the internal Glu residues unfolds in response to decreases in pH. The exact range of pH where unfolding takes place is governed by the $pK_a$ values of the internal Lys or Glu residues and by the global thermodynamic stability of the protein.

Discussion

These studies demonstrate convincingly how internal Lys and Glu residues with anomalous $pK_a$ values near physiological pH can be used to engineer pH switches, capable of undergoing large, highly cooperative conformational transitions between fully folded and unfolded states in response to small changes in pH in the physiological range. The work is rooted in previous measurements demonstrating that buried ionizable groups titrate with anomalous $pK_a$ values, many close to 7, and on understanding of fundamental principles of linkage thermodynamics.

The Δ+PHS form of SNase is too stable to be unfolded by the ionization of a single residue, but simultaneous burial of two ionizable groups with anomalous $pK_a$ was sufficient to turn the variants into pH-sensitive switches that operate near pH 7. The residues that were substituted by Lys or Glu were selected partly based on their locations, on the measured $pK_a$ values when buried singly, and on the thermodynamic consequences of the substitutions (Isom et al., Proc. Natl. Acad. Sci. U.S.A. 107: 16096-16100 (2010); Isom et al., Proc. Natl. Acad. Sci. U.S.A. 108: 5260-5265 (2011)). Because each Lys or Glu experiences a substantial shift in $pK_a$ relative to normal $pK_a$ values in water, this approach avoids the necessity of having to make many substitutions to engineer the switching behavior.

The predicted $pH_{mid}$ values based on simulations for ΔPHS/T62K/L125K and Δ+PHS/V66E/A109E were 8.0 and 5.9 to 7.0, respectively. They were within 0.5 pH units of the predicted ones (Table 3), suggesting that, at least in the case of these ionizable groups, the effects of double substitutions are nearly additive. There is no reason a priori why that should be the case.

It appears that the properties of buried Lys and Glu residues as pH sensors are not identical. The Lys side chain, being longer and more flexible, could be more difficult to bury than the shorter Glu side chain. On the other hand, the charge in the Glu side chain is delocalized, raising the possibility that burial of Glu residues is tolerated better than Lys. These studies are currently being extended to identify any existing trends in the properties of buried Lys and Glu residues as pH sensors.

The data show that the switch proteins do switch between mostly folded and mostly unfolded states. One of the potential problems that could have been encountered is with lack of cooperativity in the structural transition of interest. The protein could have resolved the electrostatic crisis represented by burial of an ionizable group with a local conformational reorganization, as suggested by NMR spectroscopy studies (Chimenti et al., Structure 20: 1071-1085 (2012); Chimenti et al., J. Mol. Biol. 405: 361-377 (2011)). The data show that the degree of unfolding differs for the two types of switch proteins. The CD spectroscopy data for the Δ+PHS/T62K/L125K variant suggests that this protein populates an intermediate state between the folded and the acid unfolded state. This state, however, is not observed in the HSQC data, because at low pH the HSQC spectra report on the unfolded state because it is the dominant population, whereas the CD and fluorescence experiments report primarily on the folded population. The data suggest consistently that at high pH the folded state is the dominant state and that at low pH the dominant state is the unfolded one.

The case of Δ+PHS/V66E/A109E is more complex. The crystal structure (FIG. 12A) shows that except for rearrangement of a loop, the native state is fully like that of the background protein. However, in pH titrations monitored by CD and fluorescence, the acid and base denatured baselines do not maintain the same signal levels. The free energy gap between the folded and base-unfolded states might be small enough to allow sporadic fluctuations to the folded state. This is consistent with the NMR data showing a predominantly unfolded population while the CD and fluorescence data betray the presence of folded protein even at high pH. The HSQC spectrum for Δ+PHS/V66E/A109E at pH 5 seems to suggest populations of folded and partially or fully-unfolded protein. The mutations may have introduced local unfolding or destabilization beyond what is detectable in a crystal structure. This is consistent with the fact that the CD wavelength scan at pH 5 does not resemble either the folded or the unfolded standard. This does not run contrary to the acid-base titration experiments as those depend on a Trp or some amount of secondary structure to be present. Overall, the data suggest that the Δ+PHS/T62K/L125K variant switches between fully folded and fully unfolded better than the Δ+PHS/V66E/A109E variant. The reasons behind these effects will be examined by engineering many other pH switches with double Lys and double Glu substitutions in SNase.

Conclusions

Lys and Glu buried in the hydrophobic interior of proteins can have anomalous $pK_a$ values because charges are incompatible with hydrophobic environments. Buried Lys and Glu can have $pK_a$ near neutral pH. Buried Lys and Glu residues with anomalous $pK_a$ values render the stability of a protein highly pH-sensitive. Thus it is possible to use buried Lys and Glu residues to engineer pH-sensing proteins that respond to a small change in pH near physiological values with a conformational change. Because the free energy difference between the buried and the water-exposed ionizable groups can be very large, one or two buried Lys or Glu residues are sufficient to drive a very large conformational transition. A transition between fully folded and fully unfolded was used in this study to illustrate general principles. Studies are underway to demonstrate how the same principles can be used to engineer switching between partially unfolded proteins, or between oligomerizing systems.

The approach for the design of pH switch proteins outlined in this study is based on general physical properties of proteins and on general thermodynamic principles. Thus, the approach is general and transferable to any other protein.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A non-naturally occurring protein comprising an artificial pH-sensitive conformational switch that responds to a change in pH, within a range of pH 5.0 to pH 9.0, by causing a cooperative unfolding transition of the protein, wherein the protein comprises two or more ionizable amino acid residues selected from Lys, Asp, and Glu, that titrate with a $pK_a$ value shifted relative to the normal $pK_a$ value in water for the one or more ionizable amino acid residues, and wherein the two or more ionizable amino acid residues comprise two or more alternative amino acid residues that have been substituted for two or more amino acid residues in an internal region of the protein.

2. The protein of claim 1, wherein the protein cooperatively unfolds within a range of pH from about 6.0 pH to about 8.0 pH.

3. The protein of claim 1, wherein the protein cooperatively unfolds within a range of pH from about 6.5 pH to about 7.5 pH.

4. The protein of claim 1, wherein the protein cooperatively unfolds in a physiological pH range.

5. The protein of claim 1, wherein the two or more alternative amino acid residues were substituted for two or more amino acid residues in an internal region of a protein having an initial thermodynamic stability of 12 kcal/mol at 298 K at pH 7.

* * * * *

UNITED STATES PATENT AND TRADEMARK OFFICE
CERTIFICATE OF CORRECTION

PATENT NO. : 10,138,471 B2
APPLICATION NO. : 14/507381
DATED : November 27, 2018
INVENTOR(S) : Garcia-Moreno et al.

Page 1 of 1

It is certified that error appears in the above-identified patent and that said Letters Patent is hereby corrected as shown below:

In the Specification

Column 1, Line 13, Replace the second paragraph as follows:
STATEMENT OF GOVERNMENTAL INTEREST
This invention was made with government support under GM073838, awarded by the National Institutes of Health. The government has certain rights in the invention.

Signed and Sealed this
Sixth Day of July, 2021

Drew Hirshfeld
*Performing the Functions and Duties of the
Under Secretary of Commerce for Intellectual Property and
Director of the United States Patent and Trademark Office*